(12) United States Patent
Wood et al.

(10) Patent No.: US 11,976,330 B2
(45) Date of Patent: May 7, 2024

(54) MIRNA SIGNATURE EXPRESSION IN CANCER

(71) Applicant: The University of Vermont and State Agricultural College, Burlington, VT (US)

(72) Inventors: Marie E. Wood, South Burlington, VT (US); Jane B. Lian, South Burlington, VT (US); Nicholas Farina, South Burlington, VT (US); Janet L. Stein, Williston, VT (US)

(73) Assignee: The University of Vermont and State Agricultural College, Burlington, VT (US)

( * ) Notice: Subject to any disclaimer, the term of this patent is extended or adjusted under 35 U.S.C. 154(b) by 130 days.

(21) Appl. No.: 16/603,182

(22) PCT Filed: Apr. 6, 2018

(86) PCT No.: PCT/US2018/026429
§ 371 (c)(1),
(2) Date: Oct. 4, 2019

(87) PCT Pub. No.: WO2018/187673
PCT Pub. Date: Oct. 11, 2018

(65) Prior Publication Data
US 2020/0123619 A1    Apr. 23, 2020

Related U.S. Application Data

(60) Provisional application No. 62/490,853, filed on Apr. 27, 2017, provisional application No. 62/482,626, filed on Apr. 6, 2017.

(51) Int. Cl.
*C12Q 1/68*     (2018.01)
*C12Q 1/686*    (2018.01)
*C12Q 1/6886*   (2018.01)

(52) U.S. Cl.
CPC ........... *C12Q 1/6886* (2013.01); *C12Q 1/686* (2013.01); *C12Q 2600/158* (2013.01); *C12Q 2600/178* (2013.01)

(58) Field of Classification Search
CPC ............... C12Q 1/6886; C12Q 1/686; C12Q 2600/158; C12Q 2600/178
See application file for complete search history.

(56) References Cited

U.S. PATENT DOCUMENTS

| | | | |
|---|---|---|---|
| 8,956,817 B2 | 2/2015 | Goel et al. | |
| 2004/0157238 A1* | 8/2004 | Quinn | C12Q 1/6827 435/6.12 |
| 2010/0203544 A1* | 8/2010 | Croce | C12N 15/1135 435/6.18 |
| 2013/0184169 A1 | 7/2013 | Klass et al. | |
| 2014/0147454 A1* | 5/2014 | Chakraborty | A61K 39/00 536/23.1 |
| 2014/0228243 A1* | 8/2014 | Smith | C12Q 1/6883 506/9 |
| 2017/0130275 A1* | 5/2017 | Kondou | C12M 1/00 |
| 2017/0233814 A1* | 8/2017 | Mounier | G01N 33/5023 506/9 |
| 2018/0230544 A1* | 8/2018 | Too | C12Q 1/6886 |

FOREIGN PATENT DOCUMENTS

JP    2015213492 A    12/2015

OTHER PUBLICATIONS

Hamam et al. MicroRNA expression profiling on individual breast cancer patients identifies novel panel of circulating microRNA for early detection. 2016, Scientific Reports, vol. 6, 25997 (Year: 2016).*
International Search Report and Written Opinion for Application No. PCT/US2018/026429 dated Aug. 1, 2018.
International Preliminary Report on Patentability for Application No. PCT/US2018/026429 dated Oct. 17, 2019.
Farina et al., Standardizing analysis of circulating microRNA: clinical and biological relevance. J Cell Biochem. May 2014;115(5):805-11. doi: 10.1002/jcb.24745.
Farina et al., Development of a predictive miRNA signature for breast cancer risk among high-risk women. Oncotarget. Nov. 28, 2017;8(68):112170-112183. doi: 10.18632/oncotarget.22750. eCollection Dec. 22, 2017.
Knyazev et al., Plasma Levels of hsa-miR-619-5p and hsa-miR-1184 Differ in Prostatic Benign Hyperplasia and Cancer. Bull Exp Biol Med. May 2016;161(1):108-11. doi: 10.1007/s10517-016-3357-7. Epub Jun. 6, 2016.
Li et al., Detection of Differentially Expressed MicroRNAs in Rheumatic Heart Disease: miR-1183 and miR-1299 as Potential Diagnostic Biomarkers. Biomed Res Int. 2015;2015:524519. doi: 10.1155/2015/524519. Epub Oct. 11, 2015.
Perdomo et al., MicroRNA 4423 is a primate-specific regulator of airway epithelial cell differentiation and lung carcinogenesis. Proc Natl Acad Sci U S A. Nov. 19, 2013;110(47):18946-51. doi: 10.1073/pnas.1220319110. Epub Oct. 24, 2013.

* cited by examiner

*Primary Examiner* — Kenneth R Horlick
(74) *Attorney, Agent, or Firm* — Wolf, Greenfield & Sacks, P.C.

(57) ABSTRACT

Methods and kits for detecting cancer-associated miRNA are disclosed herein. Methods of identifying and treating a human patient at risk for cancer are also disclosed herein.

12 Claims, 10 Drawing Sheets
Specification includes a Sequence Listing.

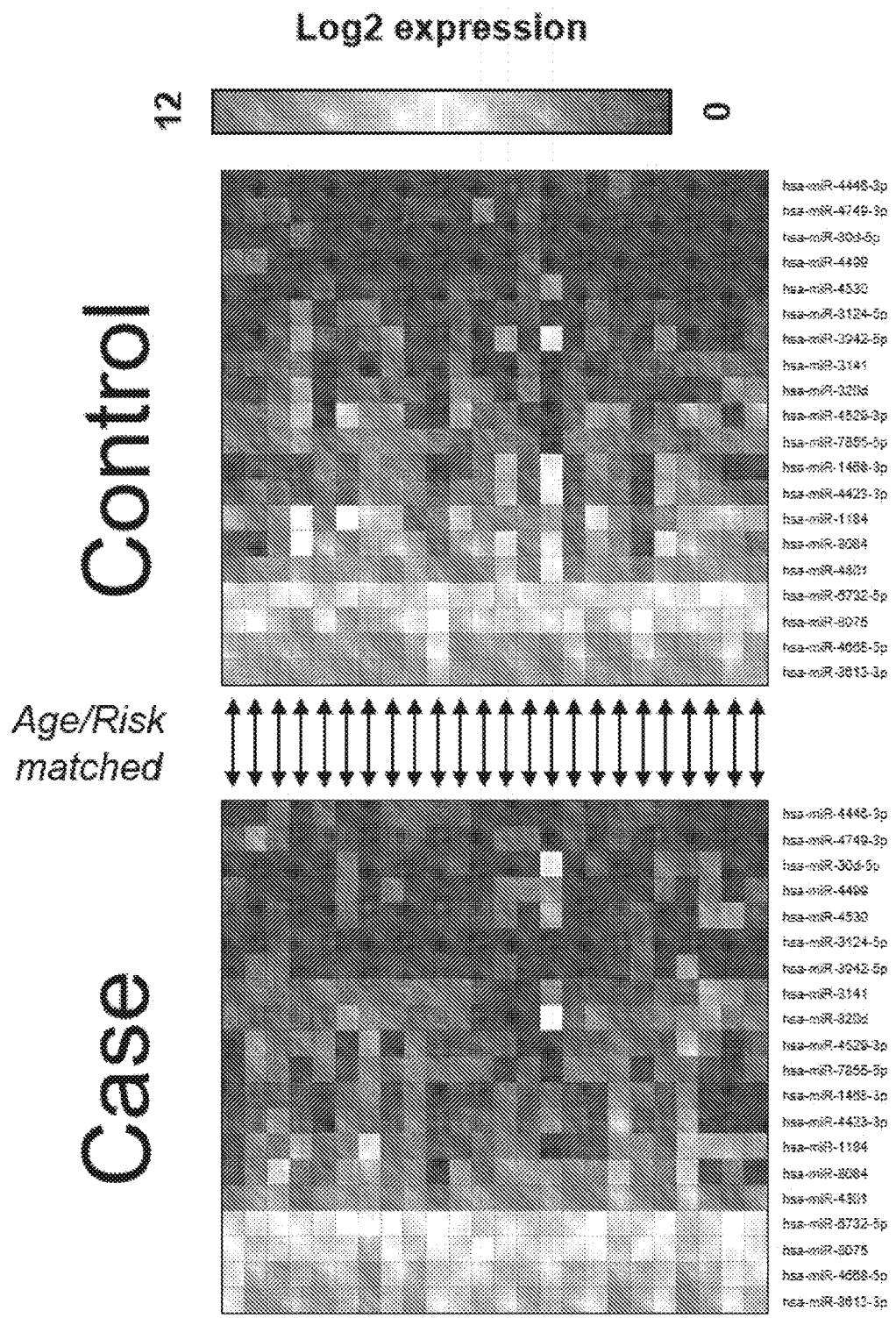

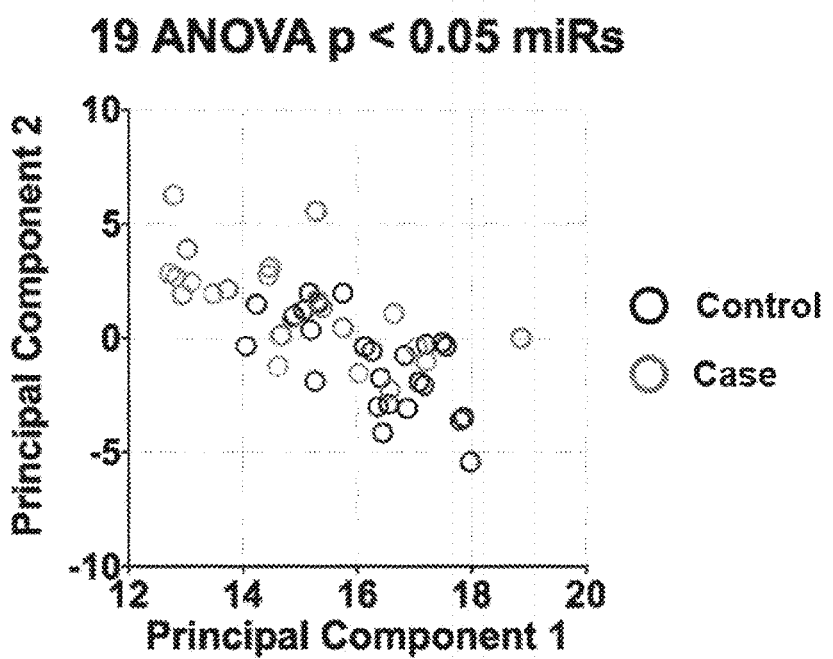

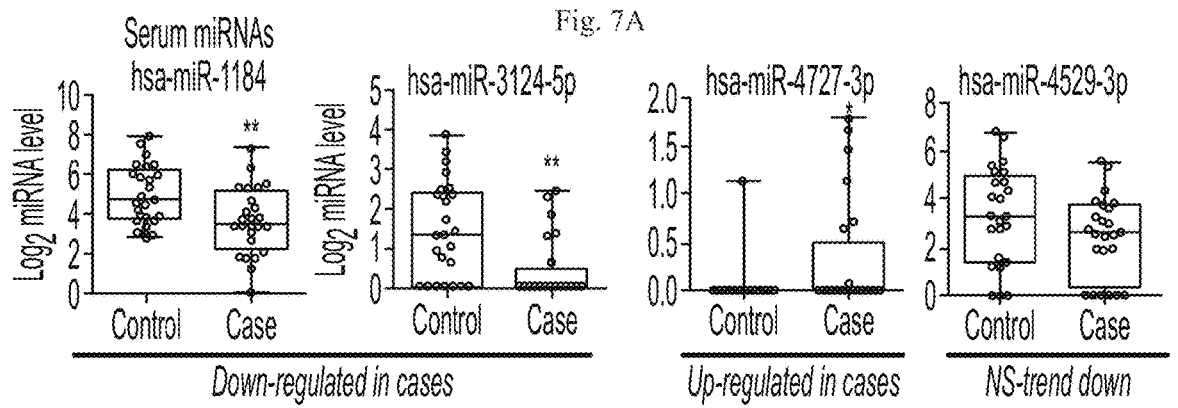
Fig. 7A
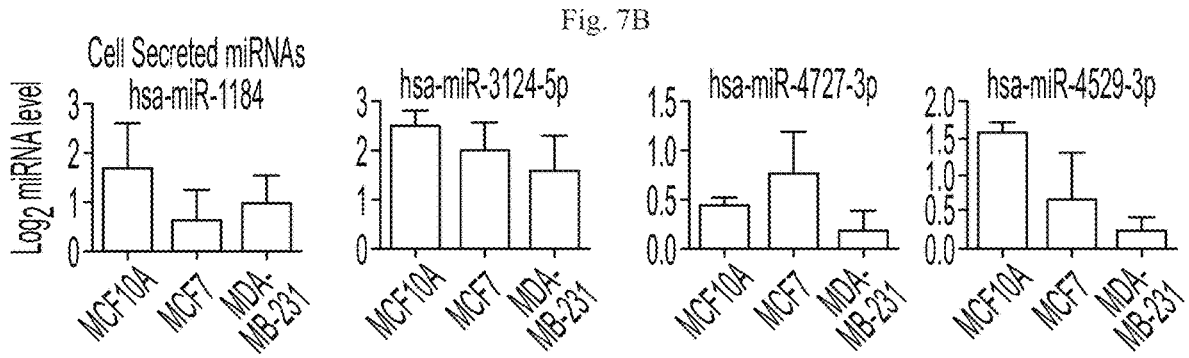
Fig. 7B
Fig. 8A
MCF10 Model of Breast Cancer Progression
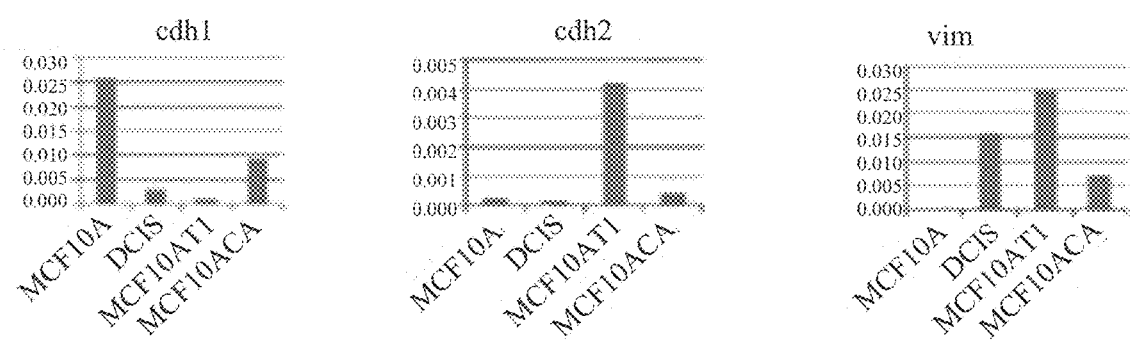

SEQUENCE LISTING

```
<160> NUMBER OF SEQ ID NOS: 25

<210> SEQ ID NO 1
<211> LENGTH: 23
<212> TYPE: RNA
<213> ORGANISM: Artificial Sequence
<220> FEATURE:
<223> OTHER INFORMATION: Synthetic Polynucleotide

<400> SEQUENCE: 1
ccugcagcga cuugauggcu ucc                                           23

<210> SEQ ID NO 2
<211> LENGTH: 23
<212> TYPE: RNA
<213> ORGANISM: Artificial Sequence
<220> FEATURE:
<223> OTHER INFORMATION: Synthetic Polynucleotide
```

```
<400> SEQUENCE: 2
ccugcagcga cuugauggcu ucc                                              23

<210> SEQ ID NO 3
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 3
agcaaaauaa gcaaauggaa aa                                               22

<210> SEQ ID NO 4
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 4
gagcuuuugg cccgguuau ac                                                22

<210> SEQ ID NO 5
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 5
aaaucucugc aggcaaaugu ga                                               22

<210> SEQ ID NO 6
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 6
uguaaacauc cccgacugga ag                                               22

<210> SEQ ID NO 7
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 7
uucgcgggcg aaggcaaagu c                                                21

<210> SEQ ID NO 8
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 8
gagggcgggu ggaggagga                                                   19

<210> SEQ ID NO 9
```

```
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 9
aaaagcuggg uugagagga                                                      19

<210> SEQ ID NO 10
<211> LENGTH: 24
<212> TYPE: RNA
<213> ORGANISM: Artificial Sequence
<220> FEATURE:
<223> OTHER INFORMATION: Synthetic Polynucleotide

<400> SEQUENCE: 10
acaaaaaaaa aagcccaacc cuuc                                                24

<210> SEQ ID NO 11
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 11
aagcaauacu guuaccugaa au                                                  22

<210> SEQ ID NO 12
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 12
auaggcacca aaaagcaaca a                                                   21

<210> SEQ ID NO 13
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 13
cagggcuggc agugacaugg gu                                                  22

<210> SEQ ID NO 14
<211> LENGTH: 17
<212> TYPE: RNA
<213> ORGANISM: Artificial Sequence
<220> FEATURE:
<223> OTHER INFORMATION: Synthetic Polynucleotide

<400> SEQUENCE: 14
aagacugaga ggaggga                                                        17

<210> SEQ ID NO 15
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 15
```
auuggacugc ugauggcccg u                                          21

<210> SEQ ID NO 16
<211> LENGTH: 18
<212> TYPE: RNA
<213> ORGANISM: Artificial Sequence
<220> FEATURE:
<223> OTHER INFORMATION: Synthetic Polynucleotide

<400> SEQUENCE: 16
cccagcagga cgggagcg                                              18

<210> SEQ ID NO 17
<211> LENGTH: 23
<212> TYPE: RNA
<213> ORGANISM: Artificial Sequence
<220> FEATURE:
<223> OTHER INFORMATION: Synthetic Polynucleotide

<400> SEQUENCE: 17
agggaaaaaa aaaaggauuu guc                                        23

<210> SEQ ID NO 18
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 18
auagugggaa gcuggcagau uc                                         22

<210> SEQ ID NO 19
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 19
cgccccuccu gcccccacag                                            20

<210> SEQ ID NO 20
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 20
uacacaagaa aaccaaggcu ca                                         22

<210> SEQ ID NO 21
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 21 uaggggugg caggcuggcc                                             20

<210> SEQ ID NO 22
<211> LENGTH: 22
<212> TYPE: RNA

```
<213> ORGANISM: Artificial Sequence
<220> FEATURE:
<223> OTHER INFORMATION: Synthetic Polynucleotide

<400> SEQUENCE: 22
acuccagccc cacagccuca gc                                                    22

<210> SEQ ID NO 23
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 23
uuggugagga ccccaagcuc gg                                                    22

<210> SEQ ID NO 24
<211> LENGTH: 24
<212> TYPE: RNA
<213> ORGANISM: Artificial Sequence
<220> FEATURE:
<223> OTHER INFORMATION: Synthetic Polynucleotide

<400> SEQUENCE: 24
ugcugauggc agaugucggg ucug                                                  24

<210> SEQ ID NO 25
<211> LENGTH: 23
<212> TYPE: RNA
<213> ORGANISM: Artificial Sequence
<220> FEATURE:
<223> OTHER INFORMATION: Synthetic Polynucleotide

<400> SEQUENCE: 25
gaauacuaag uaaaaaauca gua                                                   23
```

MIRNA SIGNATURE EXPRESSION IN CANCER

RELATED APPLICATIONS

This application is a national stage filing under 35 U.S.C. 0 371 of international application number PCT/US2018/026429, filed Apr. 6, 2018, which was published under PCT Article 21(2) in English and claims the benefit under 35 U.S.C. § 119(e) of U.S. provisional application No. 62/482,626, filed Apr. 6, 2017 and U.S. provisional application No. 62/490,853, filed Apr. 27, 2017, each of which is herein incorporated by reference in its entirety.

BACKGROUND OF THE INVENTION

Individuals vary in their risk for developing breast cancer and characterizing this risk is critical for tailoring screening and prevention strategies. Several models exist for predicting short- and long-term breast cancer risk using clinical factors such as family history, reproductive profile, and prior breast biopsy. Current models perform poorly with areas under the receiver operating characteristic curve (AUC) of 0.54-0.76, even when incorporating newer, more personalized markers such as single nucleotide polymorphisms and mammographic density. Additionally, models have significant limitations at the individual level. Biomarkers with known biological relevance for personalized risk stratification are largely undefined.

SUMMARY OF THE INVENTION

The disclosure, in some aspects, relates to a method of detecting a cancer through the presence or absence of a cancer-associated miRNA in a biological sample. The disclosure is based in some aspects on the discovery of a non-invasive microRNA-based risk-signature that distinguishes high-risk women who develop cancer years after screening from those remaining cancer-free.

In some aspects, the present disclosure includes a method of detecting the presence or absence of a cancer-associated miRNA in a biological sample by obtaining a biological sample from a human patient and detecting whether at least one cancer-associated miRNA is present in the biological sample using a nucleic acid-based detection assay, and where the cancer-associated miRNA is selected from the group consisting of hsa-miR-1184, hsa-miR-1226-5p, hsa-miR-1468-3p, hsa-miR-208a-5p, hsa-miR-216b-5p, hsa-miR-30d-5p, hsa-miR-3124-5p, hsa-miR-3141, hsa-miR-320d, hsa-miR-3613-3p, hsa-miR-3942-5p, hsa-miR-4423-3p, hsa-miR-4446-3p, hsa-miR-4499, hsa-miR-4529-3p, hsa-miR-4530, hsa-miR-4668-5p, hsa-miR-4727-3p, hsa-miR-4749-3p, hsa-miR-4801, hsa-miR-6732-5p, hsa-miR-766-3p, hsa-miR-7855-5p, hsa-miR-8075, and hsa-miR-8084. In a further embodiment, the cancer-associated miRNA is selected from the group consisting of hsa-miR-3124-5p, hsa-miR-1184, hsa-miR-4423-3p, hsa-miR-4529-3p, hsa-miR-7855-5p, and hsa-miR-4446-3p.

In some embodiments, the method further comprises detecting whether at least two cancer-associated miRNAs are present in the biological sample. In other embodiments, the method further comprises detecting whether at least three cancer-associated miRNAs are present in the biological sample. In another embodiment, the method further comprises detecting whether at least four cancer associated miRNAs are present in the biological sample. In some embodiments, the method further comprises detecting whether at least five cancer associated miRNAs are present in the biological sample. In an additional embodiment, the method further comprises detecting whether at least six cancer associated miRNAs are present in the biological sample.

In some embodiments, the human patient has at least one cancer risk factor.

In other embodiments, the cancer is breast cancer.

In another embodiment, the nucleic acid-based detection assay is an miRNA array assay. In some embodiments, the nucleic acid-based detection assay is a PCR assay. In further embodiments, the PCR assay is an RT-PCR assay or a Quantitative PCR (qPCR) assay. In some embodiments, the nucleic acid-based detection assay is a first-strand cDNA synthesis assay. In another embodiment, the nucleic acid based detection assay is a multiplex miRNA profiling assay.

In some embodiments, the method further comprises obtaining a second biological sample from the human patient 6 months to 5 years after the first biological sample is obtained and detecting the presence or absence of at least one of the cancer associated miRNA in the second biological sample, wherein the cancer associated miRNA is selected from the group consisting of hsa-miR-1184, hsa-miR-1226-5p, hsa-miR-1468-3p, hsa-miR-208a-5p, hsa-miR-216b-5p, hsa-miR-30d-5p, hsa-miR-3124-5p, hsa-miR-3141, hsa-miR-320d, hsa-miR-3613-3p, hsa-miR-3942-5p, hsa-miR-4423-3p, hsa-miR-4446-3p, hsa-miR-4499, hsa-miR-4529-3p, hsa-miR-4530, hsa-miR-4668-5p, hsa-miR-4727-3p, hsa-miR-4749-3p, hsa-miR-4801, hsa-miR-6732-5p, hsa-miR-766-3p, hsa-miR-7855-5p, hsa-miR-8075, and hsa-miR-8084.

In another embodiment, an expression level of the cancer associated miRNA is determined and the expression level is compared to a control reference level.

The present disclosure, in some aspects, includes an array comprising oligonucleotide probes that hybridize to at least two cancer associated miRNAs selected from the group consisting of hsa-miR-1184, hsa-miR-1226-5p, hsa-miR-1468-3p, hsa-miR-208a-5p, hsa-miR-216b-5p, hsa-miR-30d-5p, hsa-miR-3124-5p, hsa-miR-3141, hsa-miR-320d, hsa-miR-3613-3p, hsa-miR-3942-5p, hsa-miR-4423-3p, hsa-miR-4446-3p, hsa-miR-4499, hsa-miR-4529-3p, hsa-miR-4530, hsa-miR-4668-5p, hsa-miR-4727-3p, hsa-miR-4749-3p, hsa-miR-4801, hsa-miR-6732-5p, hsa-miR-766-3p, hsa-miR-7855-5p, hsa-miR-8075, and hsa-miR-8084 In some embodiments, the oligonucleotide probes hybridize to at least six cancer associated miRNAs.

A further aspect of the present disclosure provides a kit for detecting the presence of at least one cancer associated miRNA in a biological sample, comprising a nucleic acid specific for at least one cancer associated miRNA selected from the group consisting of hsa-miR-1184, hsa-miR-1226-5p, hsa-miR-1468-3p, hsa-miR-208a-5p, hsa-miR-216b-5p, hsa-miR-30d-5p, hsa-miR-3124-5p, hsa-miR-3141, hsa-miR-320d, hsa-miR-3613-3p, hsa-miR-3942-5p, hsa-miR-4423-3p, hsa-miR-4446-3p, hsa-miR-4499, hsa-miR-4529-3p, hsa-miR-4530, hsa-miR-4668-5p, hsa-miR-4727-3p, hsa-miR-4749-3p, hsa-miR-4801, hsa-miR-6732-5p, hsa-miR-766-3p, hsa-miR-7855-5p, hsa-miR-8075, and hsa-miR-8084, a reagent for performing a nucleic acid assay to detect the at least one cancer associated miRNA using the nucleic acid, and instructions for performing the assay to detect the at least one cancer associated miRNA. In some embodiments, the kit includes at least 6 nucleic acids for detecting at least six of the cancer associated miRNAs. In other embodiments, the kit includes 25 nucleic acids for detecting all 25 of the cancer associated miRNAs.

Another aspect of the present disclosure includes a method of identifying a human patient at risk of cancer and treating the patient, comprising: (a) obtaining a biological sample from a human patient; (b) detecting whether at least one cancer associated miRNA is present in the biological sample using a nucleic acid based detection assay, wherein the cancer associated miRNA is selected from the group consisting of hsa-miR-1184, hsa-miR-1226-5p, hsa-miR-1468-3p, hsa-miR-208a-5p, hsa-miR-216b-5p, hsa-miR-30d-5p, hsa-miR-3124-5p, hsa-miR-3141, hsa-miR-320d, hsa-miR-3613-3p, hsa-miR-3942-5p, hsa-miR-4423-3p, hsa-miR-4446-3p, hsa-miR-4499, hsa-miR-4529-3p, hsa-miR-4530, hsa-miR-4668-5p, hsa-miR-4727-3p, hsa-miR-4749-3p, hsa-miR-4801, hsa-miR-6732-5p, hsa-miR-766-3p, hsa-miR-7855-5p, hsa-miR-8075, and hsa-miR-8084; (c) identifying the patient as a patient at risk of having cancer when at least one cancer associated miRNA is present in the biological sample; and (d) administering a therapeutic regimen to the patient at risk of having cancer.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. The details of one or more embodiments of the invention are set forth in the accompanying Detailed Description, Examples, Claims, and Figures. Other features, objects, and advantages of the invention will be apparent from the description and from the claims.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIGS. 5A-5B show the graph (FIG. 5A) and heat maps (top, control; bottom, case) (FIG. 5B) of the top 20 AUC miRNAs.

FIGS. 6A-6B show the graph (FIG. 6A) and heat maps (top, control; bottom, case) (FIG. 6B) of top 19 ANOVA results miRNAs (where p<0.05 between cases and controls).

FIGS. 7A-7B show Signature miRNAs in UVM cohort (FIG. 7A) or secreted from near normal or breast cancer cell line (FIG. 7B). In FIG. 7A, circles represent serum from controls and cases within the UVM cohort. FIG. 7B shows data for 3 biological replicates (different passages) of cells grown to 90% confluency, then cultured for 24 hours in serum-free media and collected for miRNA microarray analysis detecting expressed levels normalized to background. NS=not significant.

FIGS. 8A-8C show approaches for identifying effect of signature microRNAs in near breast normal epithelial and DCIS cells. FIG. 8A shows a MCF cell progression series (top) and qPCR for EMT markers-cdh1(E), cdh2(M) and vim(M) in MCF10 series. Note DCIS cells have low E and part M properties. FIG. 8B shows the use of non-adherent culture conditions, which results in tumorsphere formation optimally by 4 days in the 3 cancer cell lines, but not in the normal 10A line (left). Quantitation of TS forming efficiency in the breast CSCs (BCSCs) from AT1 cancer cells vs non-BCSCs (p<0.001) is shown in the left panel of FIG. 8B. FIG. 8C shows CSCs can be sorted and quantitated using CD24 low/CD44high antibodies. FACS gating (top); pseudocolor density plot (dark gray, BCSC).

DETAILED DESCRIPTION OF THE INVENTION

Figure 1:
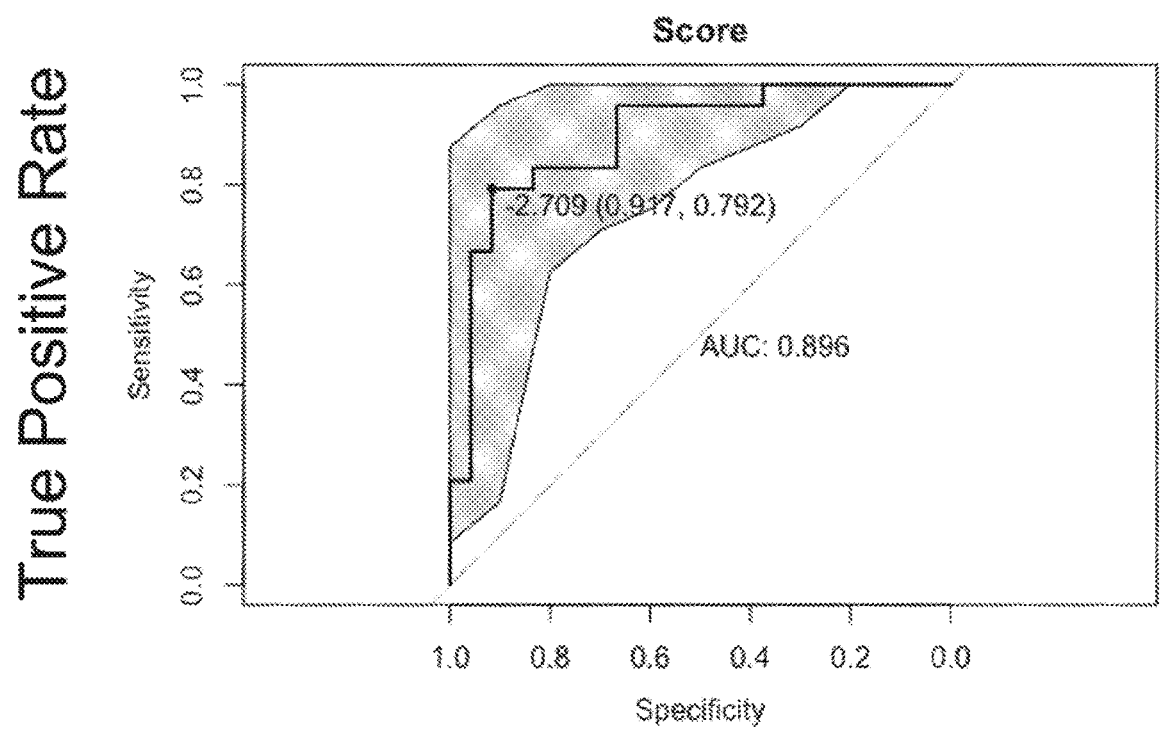
FIG. 1 shows the presently described multivariate proportional hazard model generated from data from 48 women who were at high risk for breast cancer.
Figure 2:
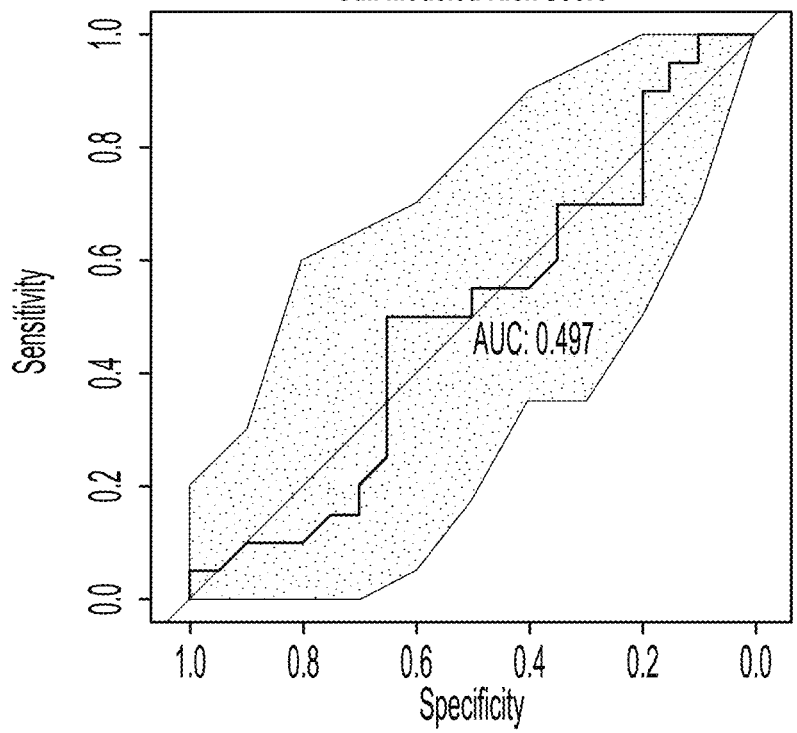
FIG. 2 shows the same data from FIG. 1 analyzed using the Gail clinical risk model.
Figure 2:
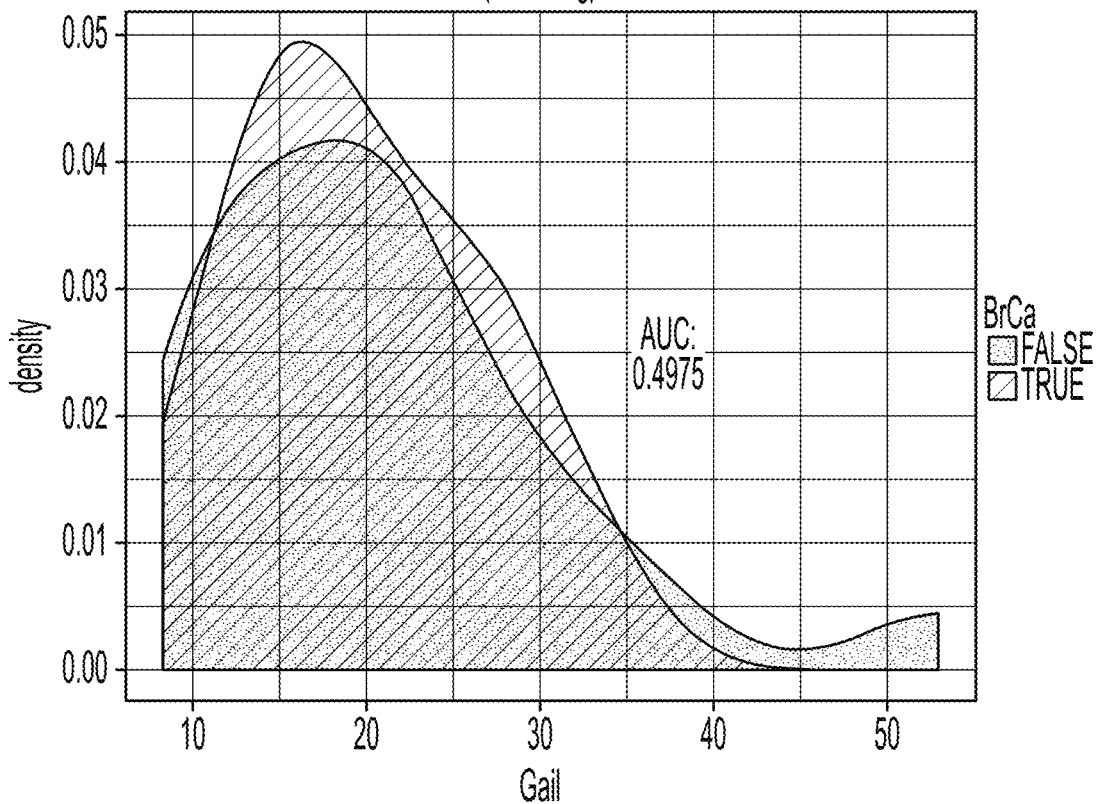

The present disclosure relates, in one aspect, to the discovery of biomarkers for predicting risk of developing cancer. In some embodiments, the present disclosure relates to methods of identifying the presence of specific biomarkers in a biological sample. In other aspects, the present disclosure relates to arrays and kits for determining whether a subject is at risk of developing cancer, thus informing and guiding treatment. miRNAs regulate cancer cell activity by modulating signaling pathways to promote disease onset and progression. Prior studies have not evaluated the potential of circulating miRNAs (c-miRNAs) as risk biomarkers that predict breast cancer development years before tumor identification.

MicroRNAs (miRNAs) are non-coding RNAs that inhibit protein expression, and are found in circulation, stable over time and easily assayed. Abnormalities in miRNAs are associated with many cancers and may represent a mechanism through which the body resists tumor onset and progression. Profiles of these circulating miRNAs (c-miRNAs) are emerging as significant cancer biomarkers especially for early detection, prognosis, and treatment. Studies have identified differences in circulating miRNA levels between cancer patients and healthy individuals. However, no study has yet evaluated the ability of c-miRNAs as risk biomarkers that predict breast cancer development years before detection. Without being bound by theory, it is thought that, for women at high-risk for breast cancer, comparison of serum miRNA expression profiles between those who do and do not develop breast cancer will identify a "risk signature" to predict future cancer development.

MicroRNA are 18-25 nucleotide long RNAs that bind to mRNA and inhibit protein expression, helping to regulate oncogenic processes such as proliferation, differentiation, and apoptosis. MicroRNAs have been shown to regulate cancer cell activity by modulating biological pathways to promote disease onset and progression. Circulating miRNAs (c-miRNAs) are released from almost all cells in many forms: in microvesicles, exosomes, bound to protein or lipid particles or unbound. As such, c-miRNAs act as intercellular signaling molecules and may function to establish local environments for initiation and progression of cancer. In breast cancer patients, serum miRNA correlates with expression in primary breast tumors.

MicroRNAs are powerful epigenetic regulators of a cell's normal function. A single miRNA can reduce expression of hundreds of genes to regulate most biological pathways in feed-forward and -back mechanisms to control cellular protein levels. While many hundreds of miRNAs are deregulated in cancer patients' tumor tissue and confirmed to support tumor progression, no study has reported miRNAs related to long term risk. FIGS. 7A-7B show examples of relationships between miRNA levels in patient serum and those secreted from cancer cells.

In 2016, an estimated 246,660 new cases of breast cancer were diagnosed in the United States with over 40,000 deaths (NCI SEER program). Individual risk for developing breast cancer varies from 8-85%. Characterizing this risk is critical for tailored screening and prevention strategies. As recommended by the United States Preventative Services Task Force (USPSTF) and American Cancer Society (ACS) women at average risk can delay initiation of screening; at moderate risk should begin annual screening earlier and will benefit from FDA-approved chemoprevention; and at highest risk are candidates for aggressive screening (with breast MRI) or surgical prevention. Screening and prevention approaches are effective but not without toxicities as breast MRI is associated with a high false-positive rate, chemoprevention carries risks of pulmonary embolism, endometrial cancer, and fracture, and surgical prevention can cause significant morbidity. It is therefore critically important that we have accurate risk assessment at the individual level where current standard practice model fail.

As described herein, an miRNA risk signature is a set of at least 2 miRNAs that are differentially expressed in a patient at risk of developing cancer, particularly breast cancer relative to a subject at low risk of cancer. miRNAs that are differentially expressed in cancer risk patients are referred to herein as cancer associated miRNAs. In some embodiments the miRNA risk signature has 2-25 cancer associated miRNAs, including but not limited to hsa-miR-1184, hsa-miR-1226-5p, hsa-miR-1468-3p, hsa-miR-208a-5p, hsa-miR-216b-5p, hsa-miR-30d-5p, hsa-miR-3124-5p, hsa-miR-3141, hsa-miR-320d, hsa-miR-3613-3p, hsa-miR-3942-5p, hsa-miR-4423-3p, hsa-miR-4446-3p, hsa-miR-4499, hsa-miR-4529-3p, hsa-miR-4530, hsa-miR-4668-5p, hsa-miR-4727-3p, hsa-miR-4749-3p, hsa-miR-4801, hsa-miR-6732-5p, hsa-miR-766-3p, hsa-miR-7855-5p, hsa-miR-8075, and hsa-miR-8084. In a further embodiment, the miRNA risk signature may comprise 2-6 of the following cancer associated miRNAs: hsa-miR-3124-5p, hsa-miR-1184, hsa-miR-4423-3p, hsa-miR-4529-3p, hsa-miR-7855-5p, and hsa-miR-4446-3p. In other embodiments the miRNA risk signature has 2-25, 2-20, 2-15, 2-10, 2-6, 2-5, 3-25, 3-20, 3-15, 3-10, 3-7, 3-6, 3-5, 3-4, 4-25, 4-20, 4-15, 4-10, 4-7, 4-6, 4-5, 5-25, 5-20, 5-15, 5-10, 5-7, 5-6, 6-25, 6-20, 6-15, 6-10, 6-7, or 6 cancer associated miRNAs.

In some embodiments it is a novel breast cancer risk assessment model for liquid biopsy, reflecting a more personalized and precise measure of long-term risk. It can discriminate eventual cases among high-risk women using blood drawn at scheduled visits many years before diagnosis, outperforming existing risk models and providing risk assessment in an actionable timeframe. The present risk signature is the first use of miRNA profiling to assess long-term breast cancer risk, and can be considered a revolutionary change from current standard practice in that the miRNA risk-signature will more accurately predict cancer development. Importantly, sample collection is non-invasive, requiring only a routine blood draw. The presently disclosed screen can be further used as a non-invasive diagnostic.

Roles of the miRNAs in the risk-signature have not been well characterized (Table 1). Current options for women at risk include adding screening MRI, chemoprevention and/or surgical prevention with bilateral mastectomy+/−prophylactic oophorectomy. While each of these options has been shown to improve early detection and risk; they have significant side effects and toxicities which negatively impact uptake. New options with fewer potential complications would substantially improve the medical management of high-risk women.

It is thought that the present risk signature is the first use of miRNA profiling to assess long-term breast cancer risk. Several miRNAs in the risk signature have not previously been associated with cancer; and the function of 1 has not yet been identified (Table1). Additionally, the miRNA risk signature is a novel breast cancer risk assessment model, reflecting a more personalized and precise measure of long term risk. The risk signature can discriminate eventual cases among high-risk women using blood drawn many years before diagnosis; it outperforms existing risk models in the high-risk population and provides risk assessment in an actionable timeframe.

Cancer-Associated miRNAs

As described herein, a variety of miRNAs may be differentially present in subjects at risk for cancer. A "cancer-associated miRNA" is a miRNA whose level is modulated in a subject likely to develop cancer compared to the level of a subject not likely to develop cancer. The differences in levels of miRNA are statistically significant. Examples of cancer-associated miRNAs include, but are not limited to, hsa-miR-1184, hsa-miR-1226-5p, hsa-miR-1468-3p, hsa-miR-208a-5p, hsa-miR-216b-5p, hsa-miR-30d-5p, hsa-miR-3124-5p, hsa-miR-3141, hsa-miR-320d, hsa-miR-3613-3p, hsa-miR-3942-5p, hsa-miR-4423-3p, hsa-miR-4446-3p, hsa-miR-4499, hsa-miR-4529-3p, hsa-miR-4530, hsa-miR-4668-5p, hsa-miR-4727-3p, hsa-miR-4749-3p, hsa-miR-4801, hsa-miR-6732-5p, hsa-miR-766-3p, hsa-miR-7855-5p, hsa-miR-8075, and hsa-miR-8084. Their respective accession numbers and sequences, from miRBase.org, are given in Table 5. Examples of breast cancer-associated miRNAs include, but are not limited to hsa-miR-3124-5p, hsa-miR-1184, hsa-miR-4423-3p, hsa-miR-4529-3p, hsa-miR-7855-5p, and hsa-miR-4446-3p. In some embodiments, a patient is identified to be at risk of having cancer when at least one cancer-associated miRNA is detected in the biological sample. In a further embodiment, the patient identified to be at risk of having cancer is administered a therapeutic regimen. Therapeutic regimens may include, for example, chemotherapy, radiation, or surgery.

Accordingly, some aspects of the disclosure relate to methods of detecting the presence or absence of a cancer-associated miRNA in a biological sample. The method comprises obtaining a biological sample from a human patient and detecting whether at least one cancer-associated miRNA is present in the sample using a nucleic acid-based detection assay. In some embodiments, 2, 3, 4, 5, 6, 7, 8, 9, 10, 11, 12, 13, 14, 15, 16, 17, 18, 19, 20, 21, 22, 23, 24 or all 25 miRNAs will be present in the sample. In other embodiments, 2, 3, 4, 5, or all 6 of the breast cancer-associated miRNAs will be present in the sample.

The human patient may be at risk of having cancer, for example, the human patient may have one or more cancer risk factors. Cancer risk factors include, but are not limited to, hereditary risk factors, age, alcohol, exposure to cancer-causing substances, chronic inflammation, diet, hormones, immunosuppression, infectious agents, obesity, radiation, sun exposure, and tobacco use. Other risk factors will be apparent to the skilled artisan.

The human patient may be at risk of having breast cancer, The miRNAs may also be involved in other cancers, including, but not limited to, acute granulocytic leukemia, acute lymphocytic leukemia (ALL), acute myelogenous leukemia (AML), adenocarcinoma, adenosarcoma, adrenal cancer, adrenocortical carcinoma, anal cancer, anaplastic astrocytoma, angiosarcoma, appendix cancer, astrocytoma, basal cell carcinoma, B cell lymphoma, bile duct cancer, bladder cancer, bone cancer, bone marrow cancer, bowel cancer, brain cancer, brain stem glioma, breast cancer, cervical cancer, cholangiocarcinoma, chondrosarcoma, chronic lymphocytic leukemia (CLL), chronic myelogenous leukemia (CML), colon cancer, colorectal cancer, craniopharyngioma, cutaneous lymphoma, cutaneous melanoma, diffuse astrocytoma, ductal carcinoma in situ (DCIS), endometrial cancer, ependymoma, epithelioid sarcoma, esophageal cancer, Ewing sarcoma, extrahepatic bile duct cancer, eye cancer, fallopian tube cancer, fibrosarcoma, gallbladder cancer, gastric cancer, gastrointestinal cancer, gastrointestinal carcinoid cancer, gastrointestinal stromal tumors GIST), glioblastoma multiforme (GBM), glioma, hairy cell leukemia, head and neck cancer, hemangioendothelioma, Hodgkin lymphoma, hypopharyngeal cancer, infiltrating ductal carcinoma (IDC), infiltrating lobular carcinoma (ILC), inflammatory breast cancer, intestinal cancer, intrahepatic bile duct cancer, islet cell cancer, jaw cancer, Kaposi sarcoma, kidney cancer, laryngeal cancer, leiomyosarcoma, leptomeningeal metastases, leukemia, lip cancer, liposarcoma, liver cancer, lobular carcinoma in situ, low-grade astrocytoma, lung cancer, lymph node cancer, lymphoma, medullary carcinoma, medulloblastoma, melanoma, meningioma, Merkel cell carcinoma, mesenchymal chondrosarcoma, mesothelioma, metastatic breast cancer, metastatic melanoma, metastatic squamous neck cancer, mixed gliomas, mouth cancer, mucinous carcinoma, mucosal melanoma, multiple myeloma, myelodysplastic syndrome, nasal cavity cancer, nasopharyngeal cancer, neck cancer, neuroblastoma, Non-Hodgkin lymphoma (NHL), non-small cell lung cancer (NSCLC), oat cell cancer, ocular cancer, ocular melanoma, oligodendroglioma, oral cancer, oral cavity cancer, oropharyngeal cancer, osteogenic sarcoma, osteosarcoma, ovarian cancer, ovarian epithelial cancer, ovarian germ cell tumor, ovarian primary peritoneal carcinoma, ovarian sex cord stromal tumor, Paget's disease, pancreatic cancer, papillary carcinoma, paranasal sinus cancer, parathyroid cancer, pelvic cancer, penile cancer, peripheral nerve cancer, peritoneal cancer, pharyngeal cancer, pheochromocytoma, pilocytic astrocytoma, pineal region tumor, pineoblastoma, pituitary gland cancer, primary central nervous system (CNS) lymphoma, prostate cancer, rectal cancer, renal cell carcinoma, renal pelvis cancer, rhabdomyosarcoma, salivary gland cancer, sarcoma, sinus cancer, skin cancer, small cell lung cancer (SCLC), small intestine cancer, soft tissue sarcoma, spinal cancer, spinal column cancer, spinal cord cancer, squamous cell carcinoma, stomach cancer, synovial sarcoma, T cell lymphoma, testicular cancer, throat cancer, thymoma/thymic carcinoma, thyroid cancer, tongue cancer, tonsil cancer, transitional cell cancer, triple-negative breast cancer, tubal cancer, tubular carcinoma, ureteral cancer, uterine adenocarcinoma, uterine cancer, uterine sarcoma, vaginal cancer, and vulvar cancer.

The methods may involve obtaining a biological sample from the subject. As used herein, the phrase "obtaining a biological sample" refers to any process for directly or indirectly acquiring a biological sample from a human patient. For example, a clinical sample may be obtained (e.g., at a point-of-care facility, a physician's office, a hospital) by procuring a tissue or fluid sample (e.g., blood draw, spinal tap) from a human patient. Alternatively, a biological sample may be obtained by receiving the biological sample (e.g., at a laboratory facility) from one or more persons who procured the sample directly from the human patient.

In some embodiments, a first and second biological sample is obtained from the subject. The time between obtaining samples may be six months or less. In some embodiments, the time between obtaining samples is five years or longer. In certain embodiments, the time between obtaining samples is 6 months, 8 months, 10 months, 1 year, 1.5 years, 2 years, 2.5 years, 3 years, 3.5 years, 4 years, 4.5 years, or 5 years. In some embodiments, the time between obtaining the first biological sample and obtaining the second biological sample the human patient is a time sufficient for a change in cancer status to occur in the individual.

The term "biological sample" refers to a sample derived from a subject, e.g., a patient. Biological samples include, but are not limited to tissue (e.g., brain tissue), cerebrospinal fluid, blood, blood fractions (e.g., serum, plasma), sputum, fine needle biopsy samples, urine, peritoneal fluid, and pleural fluid, or cells therefrom (e.g., blood cells (e.g., white blood cells, red blood cells)). Accordingly, a biological sample may comprise a tissue, cell or biomolecule (e.g., RNA, protein). In some embodiments, the biological sample is a sample of peripheral blood, serum, cerebrospinal fluid, urine and tissue.

Examples of assays used to measure miRNA presence, but are not limited to hybridization-based assays. Hybridization-based assay are well known in the art, and include, but are not limited to, an oligonucleotide array assay (e.g., miRNA array assays), an oligonucleotide conjugated bead assay (e.g., Multiplex Bead-based Luminex® Assays), a molecular inversion probe assay, a serial analysis of gene expression (SAGE) assay, northern blot assay, an in situ hybridization assay, cDNA array assays RNase protein assays, or a PCR assay. In some embodiments, the PCR assay is an RT-PCR assay or a quantitative PCR (qPCR) assay. In some embodiments, the nucleic acid-based detection assay is a first-strand cDNA synthesis assay. Multiplex systems, such as oligonucleotide arrays or bead-based nucleic acid assay systems are particularly useful for evaluating levels and/or the presence of a plurality of nucleic acids in simultaneously. For example, multiplex miRNA profiling assays are used in some embodiments. RNA-Seq (mRNA sequencing using Ultra High throughput or Next Generation Sequencing) may also be used to determine expression levels. Other appropriate methods for determining levels of nucleic acids will be apparent to the skilled artisan.

The expression level of one or more cancer-associated miRNAs may be determined as the level of protein targeted by the miRNA. Examples of assays to measure protein levels include, but are not limited to, antibody-based assays. Antibody-based assays are well known in the art and include, but are not limited to, antibody array assays, antibody conjugated-bead assays, enzyme-linked immuno-sorbent (ELISA) assays, immunofluorescence microscopy assays, and immunoblot assays. Other methods for determining protein levels include mass spectroscopy, spectrophotometry, and enzymatic assays. Still other appropriate methods for determining levels of proteins will be apparent to the skilled artisan.

It is to be understood that a biological sample may be processed in any appropriate manner to facilitate determining expression levels of cancer-associated miRNAs. For example, biochemical, mechanical and/or thermal processing methods may be appropriately used to isolate a biomolecule of interest, e.g., miRNA, from a biological sample. A miRNA sample may be isolated from a clinical sample by processing the biological sample using methods well known in the art and levels of an miRNA may be determined in the biological sample.

The methods disclosed herein also typically comprise comparing expression pattern of cancer-associated miRNAs with an appropriate reference expression pattern. An appropriate reference expression pattern can be determined or can be a pre-existing reference expression pattern. An appropriate reference expression pattern may be a threshold expression level of cancer-associated miRNAs such that an expression level that is above or below the threshold level is indicative of cancer risk in a human patient. In some embodiments, the appropriate reference expression pattern comprises standard expression levels of the cancer-associated miRNAs.

An appropriate reference expression pattern may be an expression pattern indicative of a subject that is at low risk of cancer. For example, an appropriate reference expression pattern may be representative of the expression level of a particular cancer-associated miRNA in a biological sample obtained from a subject who does not have cancer and who did not develop cancer over a certain period of time following sample procurement. The period of time may be from one to 40 years, including 1, 2, 3, 4, 5, 6, 7, 8, 9, 10, 12, 14, 16, 18, 20, 22, 24, 26, 28, 30, 32, 34, 36, 38, or 40 years. When an appropriate reference expression pattern is indicative of a subject who is at low risk of cancer, a significant difference between an expression pattern determined from a subject in need of risk prediction of cancer and the appropriate reference expression pattern may be indicative of risk of cancer in the subject. Alternatively, when an appropriate reference expression pattern is indicative of the subject having low risk of cancer, a lack of a significant difference between an expression pattern determined from a subject in need of risk prediction of cancer and the appropriate reference expression pattern may be indicative of the individual having low risk of cancer.

The magnitude of difference between an expression pattern and an appropriate reference expression pattern may vary. For example, a significant difference that indicates risk of cancer may be detected when the expression level of a cancer-associated miRNA in a biological sample is at least 1%, at least 5%, at least 10%, at least 25%, at least 50%, at least 100%, at least 250%, at least 500%, or at least 1000% higher, or lower, than an appropriate reference level of that miRNA. Similarly, a significant difference may be detected when the expression level of a cancer-associated miRNA in a biological sample is at least 2-fold, at least 3-fold, at least 4-fold, at least 5-fold, at least 6-fold, at least 7-fold, at least 8-fold, at least 9-fold, at least 10-fold, at least 20-fold, at least 30-fold, at least 40-fold, at least 50-fold, at least 100-fold, or more higher, or lower, than the appropriate reference level of that miRNA. Significant differences may be identified by using an appropriate statistical test. Tests for statistical significance are well known in the art and are exemplified in Applied Statistics for Engineers and Scientists by Petruccelli, Chen and Nandram 1999 Reprint Ed. It is to be understood that a plurality of expression levels may be compared with plurality of appropriate reference levels, e.g., on an miRNA-miRNA basis, in order to assess the cancer risk. In such cases, Multivariate Tests, e.g., Hotelling's T2 test, may be used to evaluate the significance of observed differences. Such multivariate tests are well known in the art and are exemplified in Applied Multivariate Statistical Analysis by Richard Arnold Johnson and Dean W. Wichern Prentice Hall; 4th edition (Jul. 13, 1998).

Further aspects of the present disclosure include an array comprising oligonucleotide probes that hybridize to at least two cancer-associated miRNAs, which are useful for determining levels of multiple nucleic acids simultaneously. In some embodiments, the nucleic acid arrays comprise, or consist essentially of, binding probes for cancer-associated miRNAs of at least 2, at least 3, at least 4, at least 5, or all six miRNAs in Table 1. In other embodiments, the nucleic acid arrays comprise, or consist essentially of, binding probes for cancer miRNAs of at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, or all 25 miRNAs in Table 5. Such arrays may be obtained or produced from commercial sources. Methods for producing nucleic acid arrays are well known in the art. For example, nucleic acid arrays may be constructed by immobilizing to a solid support large numbers of oligonucleotides, polynucleotides, or cDNAs capable of hybridizing to nucleic acids corresponding to miRNAs, or portions thereof. The skilled artisan is also referred to Chapter 22 "Nucleic Acid Arrays" of Current Protocols In Molecular Biology (Eds. Ausubel et al. John Wiley and #38; Sons NY, 2000), International Publication WO00/58516, U.S. Pat. Nos. 5,677,195 and 5,445,934 which provide non-limiting examples of methods relating to nucleic acid array construction and use in detection of nucleic acids of interest.

Kits comprising reagents for detecting the presence or absence of at least one cancer-associated miRNA from the biological sample are also provided. In some embodiments, the kit may include reagents to detect 2, 3, 4, 5, or all six of the cancer-associated miRNAs listed in Table 1. In additional embodiments, the kit may include at least six nucleic acids to detect all six of the cancer-associated miRNAs in Table 1. In other embodiments, the kit may include reagents to detect 2, 3, 4, 5, 6, 7, 8, 9, 10, 11, 12, 13, 14, 15, 16, 17, 18, 19, 20, 21, 22, 23, 24, or all 25 of the cancer-associated miRNAs listed in Table 5. In further embodiments, the kit may include at least 25 nucleic acids to detect all 25 of the cancer-associated miRNAs in Table 5. Kits may include a package housing one or more containers with reagent for measuring the presence or expression pattern of at least one cancer-associated miRNA from the biological sample and instructions for determining the expression patterns of the at least one cancer-associated miRNA and comparing the expression pattern with an appropriate reference expression pattern of the at least one cancer-associated miRNA. Kits comprising the nucleic acid-based assays, including oligonucleotide arrays described herein are also included.

EXAMPLES

In order that the invention described herein may be more fully understood, the following examples are set forth. The examples described in this application are offered to illustrate the compounds, pharmaceutical compositions, and methods provided herein and are not to be construed in any way as limiting their scope.

Example 1. A Novel, miRNA-Based Liquid Biopsy Predictive of Long-Term Breast Cancer Risk A non-invasive microRNA-based risk-signature that distinguishes high-risk women who develop cancer years after screening from those remaining cancer-free has been developed. The High Risk Breast Program (HRBP), established at the University of Vermont in 2003, is comprised of over 600 women at moderate/high risk of developing breast cancer and has a median follow-up of 8.9 years. Yet, less than 10% of enrolled women have since been diagnosed. Enrolled women provide clinical data and serum samples at baseline and every 4 years thereafter. Twenty-four women who had developed breast cancer (cases) and matched cancer-free controls on age and reason for high-risk status (i.e., strong family history or benign breast disease). Participant characteristics are given in Table 2 and the pathologic features of the 24 women who developed breast cancer are given in Table 3. Using a standardized protocol (Farina et al. 2014, J Cell Biochem), 2578 human microRNAs (miRNAs) (all the known human miRNAs at the time) were profiled in serum collected from these women well before breast cancer diagnosis (mean, 3.2 years; range 0.6-8.7 years) using microarray technology (Affymetrix microRNA v4.0 microarray). Nearly 80% (19/24) of these women were diagnosed more than 15 months after serum collection. The 24 controls had been followed for a median of 10.3 years (rnage 4.0-13.2 years) since serum collection, and remain cancer-free.

From this global expression screen, 25 miRNAs that distinguish cases from controls based on significant (ANOVA p<0.05) differential expression and individual miRNA classification performance were identified (Table 5) using a standardized method for serum miRNA expression analysis, encompassing all sets from RNA isolation through generation of background normalized data (specifically, RNA isolation, miRNA profiling, probe summarization, data processing and then AUC and ANOVA analysis). To confirm the method, two different serum aliquots collected at the same time from the same woman were processed independently by different individuals and a 1:1 correlation was obtained post-normalization as opposed to disparate raw data (data not shown).

Figure 5A:
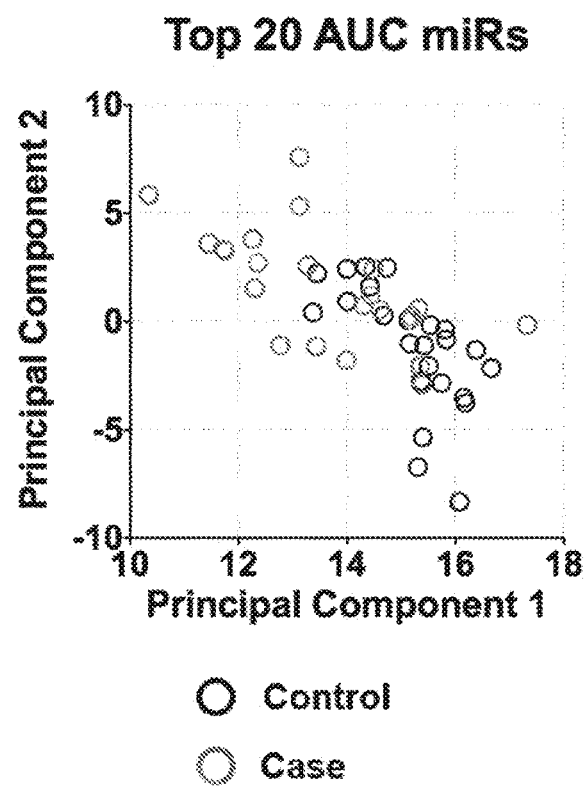
Figure 6B:
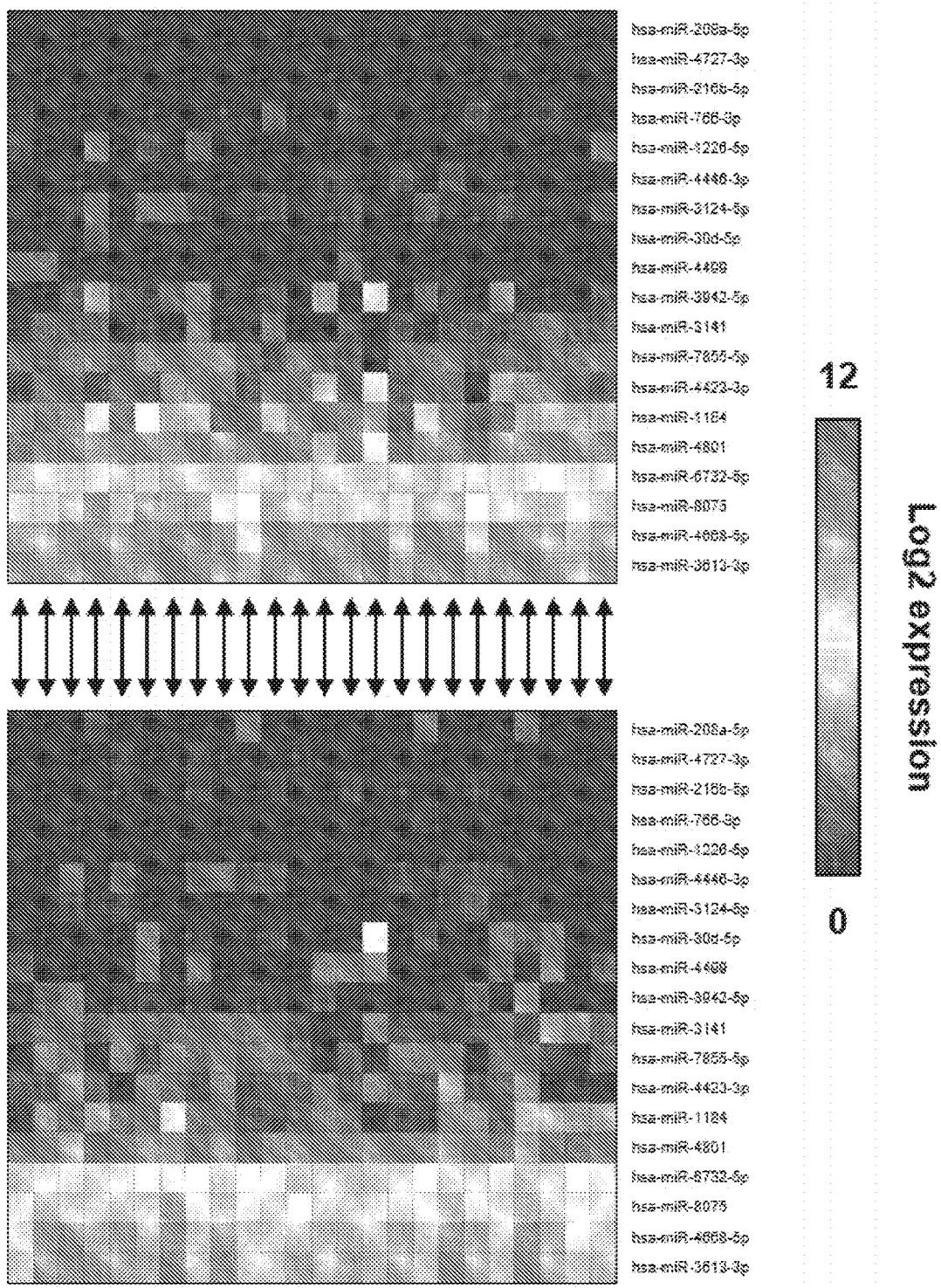

Candidate miRNAs were selected for further development of a risk signature using two distinct techniques: area under the ROC curves (AUC) and an analysis of variance (ANOVA) p-value. AUC, a measurement of classification accuracy, and associated 95% confidence intervals were generated for each of the 2578 interrogated miRNAs (data not shown). Twenty miRNAs with the highest individual AUC, ranging from 0.632 to 0.766, were selected for further analysis. In parallel, the ANOVA p-value was calculated for each miRNA between cases and controls (data not shown). Nineteen miRNAs were identified as having a p<0.05. Combined, there were 25 unique miRNAs identified: 14 in common between the two analyses, 6 unique to the AUC analysis, and 5 unique to the ANOVA analysis. Principal component analysis using the expression of the two miRNA sets identified under different analyses showed segregation of cases and controls; in general, cases cluster to the upper left quadrant while controls trend to the lower right (FIGS. 5A and 6A). The levels of many candidate miRNAs were found to be reduced in serum of women that ultimately developed breast cancer, suggesting a role for these miRNAs in breast cancer risk.

The identified 25 candidate miRNAs (FIGS. 5B and 6B) were used to develop a risk score. A bidirectional stepwise regression Cox proportional hazards (CoxPH) model was utilized to identify those miRNAs that, when combined, best distinguished cases from controls. Computational methods were used to account for the limited size of the patient database. Specifically, the 48 patients were randomly divided into a training set of 32 samples and a validation set of 16 samples and 1000 individual models were generated. For each miRNA set (AUC or ANOVA set), a CoxPH model was built using only the expression levels of miRNAs from each set in the randomly selected patient training set (n=32). The model was then tested on the remaining patient validation set (n=16) and evaluated by the AUC. Note than nearly 70 billion possible combinations existed in selecting the training and validation sets. Candidate signature miRNAs were model-selected based on AIC and refined by 2 criteria: presence in over 500 models and presence in over 50% of the models with an AUC>0.8 in the validation patient set. Nine out of 25 miRNAs passed these thresholds with each miRNA set containing 6 miRNAs. Three miRNAs (hsa-miR-1184, hsa-miR-4423-3p, and hsa-miR-7855-5p) were common to both the AUC and ANOVA sets.

Final models were generated separately for the top model-selected miRNAs, 6 for AUC and 6 for ANOVA, utilizing expression levels across all 48 patients. Each set of 5 miRNAs was added to the algorithm and ROC curves were generated. While all 6 miRNAs in the AUC set were used to generate a risk score, hsa-miR-7855-5p was computationally excluded in the ANOVA set, based on AIC model selection, as the addition of this miRNA did not improve the model in ability to classify patient outcome. The miRNA-modeled risk scores performed well at classifying cases, with AUC and 95% confidence intervals of 0.896 (0.804-0.988) and 0.870 (0.771-0.970). The models generated the following risk score formulas:

Formula 1:
AUC- selected miRNA-modeled risk score:
$$\text{Risk score}=(-1.062 \times hsa\text{-}miR\text{-}3124\text{-}5p)+(-0.32 \times hsa\text{-}miR\text{-}1184)+(-0.33 \times hsa\text{-}miR\text{-}4529\text{-}3p)+(-0.626 \times hsa\text{-}miR\text{-}7855\text{-}5p)+(0.359 \times hsa\text{-}miR\text{-}4446\text{-}3p)$$

Formula 2:
ANOVA- selected miRNA-modeled risk score:
$$\text{Risk score}=(-0.274 \times hsa\text{-}miR\text{-}1184)+(-1.305 \times hsa\text{-}miR\text{-}766\text{-}3p)+(-0.393 \times hsa\text{-}miR\text{-}4432\text{-}3p)+(0.601 \times hsa\text{-}miR\text{-}4727\text{-}3p)+(0.229 \times hsa\text{-}miR\text{-}208a\text{-}5p)$$

These formula-generated risk scores were applied to miRNA levels from each case and control for discriminatory power. The data demonstrate that the risk scores distinguish cases form controls, for example, in a model-calculated threshold (data not shown). The threshold may be used to identify women who are at significant risk for developing breast cancer. Associated model statistics are shown in Table 4. Note that the panel of 6 miRNAs outperforms current clinical models in high-risk women (FIG. 1; AUC=0.896 compared with Gail model AUC=0.497; Claus model AUC=0.507; IBIS model AUC=0.503). Additionally, the miRNAs in this signature perform better together than alone (Table 1).

The expression of all model-identified miRNAs (n=9) used for the risk score calculation was further evaluated in all 48 samples. Two-thirds of these miRNAs (hsa-miR-3124-5p, hsa-miR-1184, hsa-miR-4423-3p, hsa-miR-4529-3p, hsa-miR-7855, and hsa-miR-766-3p) tended to have lower expression levels in cases, as compared to controls (data not shown). Conversely, hsa-miR-4446-3p, hsa-miR-4727-3p, and has-miR-208a-5p were detected at elevated levels in cases, compared to controls (data not shown). The three miRNAs unique to the ANOVA set (hsa-miR-766-3p, hsa-miR-4727-3p, and hsa-miR-208a-5p) were detected in less than 25% of patients, and were eliminated from the final risk signature.

Biologic Pathway Analysis

Biologic pathway analysis for modeled miRNAs revealed roles in many cancer-related pathways and biological functions including: regulation of EMT, molecular mechanisms of cancer, and malignant solid tumor. The analysis was focused on the 6 miRNAs frequently detected in the serum of at-risk women that were also identified from the AUC-selected miRNA set. The interaction networks of hsa-miR-3124-5p, hsa-miR-1184, hsa-miR-4423-3p, hsa-miR-4529-3p, hsa-miR-7855-5p, and hsa-miR-4446-3p were identified via Ingenuity Pathway Analysis (IPA; ingenuity.com). No targets exist within IPA for hsa-miR-7855-5p, so it was excluded from pathway analysis. The comparison analysis feature in IPA was used to identify biological pathways regulated by the remaining 5 miRNAs in combination. Regulation of the epithelial-mesenchymal transition pathway, VEGF signaling, and molecular mechanisms of cancer were within the top 5 Ingenuity Canonical Pathways, indicating enrichment in genes targeted by risk signature miRNA in cancer-related biological processes. Further, all of the top 5 enriched diseases and biological functions are directly tied to cancers. The difference in these risk-associated miRNAs and predicted deregulated pathways may predispose women to develop breast cancer, providing both novel biomarkers as well as insight into avenues for breast cancer prevention.

Validation of the miRNA Risk Signature

The miRNA-based predictive score for breast cancer incidence among high risk women will be validated in a larger, independent study population. The Canadian Cancer Trials Group (CCTG) has banked serum from the MAP.3 clinical trial and has agreed to provide samples from the placebo arm of this trial. The CCTG MAP.3 trial is a 4560 person randomized placebo-controlled trial of exemestane for 5 years in high-risk women. All women were postmenopausal at enrollment, age 35 or older, and had at least one major breast cancer risk factor (age ≥60, Gail score >1.66%, history of atypical ductal or lobular hyperplasia, lobular carcinoma in situ, or history of ductal carcinoma in situ (DCIS) with mastectomy). Women were excluded if they carried a pathogenic variant in BRCA1 or BRCA2, or if they had been treated for DCIS with lumpectomy. With a median follow-up of 3.0 years, 51 women have developed breast cancer. Sera was collected in a standardized fashion and frozen in 2 ml aliquots. These samples have not been thawed, which is important for miRNA analysis as has been previously demonstrated. Sera from women in the placebo arm are being made available by the CCTG, and access to clinical data has been made possible through consultation with members of the MAP.3 study team.

The CCTG MAP.3 placebo arm consists of 2,275 women with no history of malignancy. From this source population all cases of incident invasive breast cancer will be enrolled (n=39). For each case, a list of potential controls who match the case on age group (defined in 5-year intervals) and reason(s) for high-risk status will be enumerated. The list of controls will be compiled from the baseline roster of participants in the placebo arm. Potential controls in each list will be assigned a random number drawn from a uniform distribution on the interval [0, 1], and the lists will be sorted on this number. The top two controls in each sorted list will be matched to the case. Should a control turn out to be unsuitable for enrollment (e.g., due to insufficient or hemolyzed blood samples), another control will be selected in order from the list. It is expected that 39 cases and 78 individually matched controls will be enrolled, for a total study size of 117 subjects.

The expression levels of 25 high performing miRNAs in cases/controls on the placebo arm of CCTG MAP.3 will be determined (117 cases and controls on the placebo arm) using qPCR. Then, the classification performance of the 6 miRNA signature will be validated in the new cohort. Next, the predictive performance of the miRNA signature will be refined by applying a forward selection procedure based on changes in AUC to evaluate the contribution of additional miRNAs from the 19 remaining candidates identified in the earlier cohort.

Discussion

Using samples obtained from women years prior to being diagnosed with breast cancer and an iterative strategy for modeling, a miRNA signature of breast cancer risk has been identified. The tested miRNA signature (6 miRNA) distinguished cases from controls in a cohort of clinically similar high-risk women. Additionally, the miRNAs taken together were more informative then any single miRNA. Some of the miRNAs in this signature are involved in many cancer-related pathways. This appears to be the first signature of breast cancer risk using circulating miRNAs and may represent an important "liquid biopsy" for identification of women at greatest risk for developing breast cancer. Additionally, the functions of the miRNAs in the signature may identify novel targets for prevention strategies.

Figure 3:
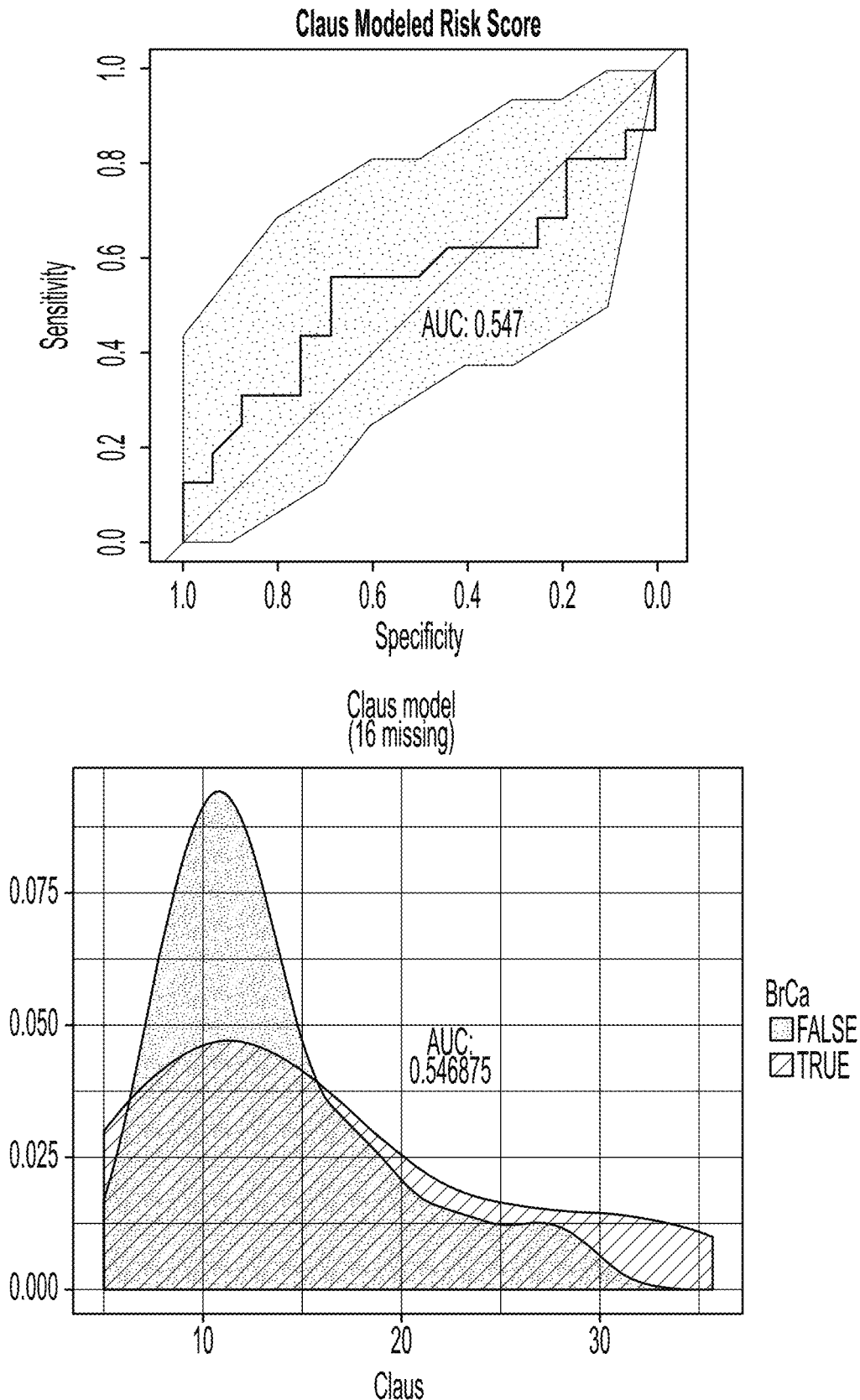
FIG. 3 shows the same data from FIG. 1 analyzed using the Claus clinical risk model.
Figure 4:
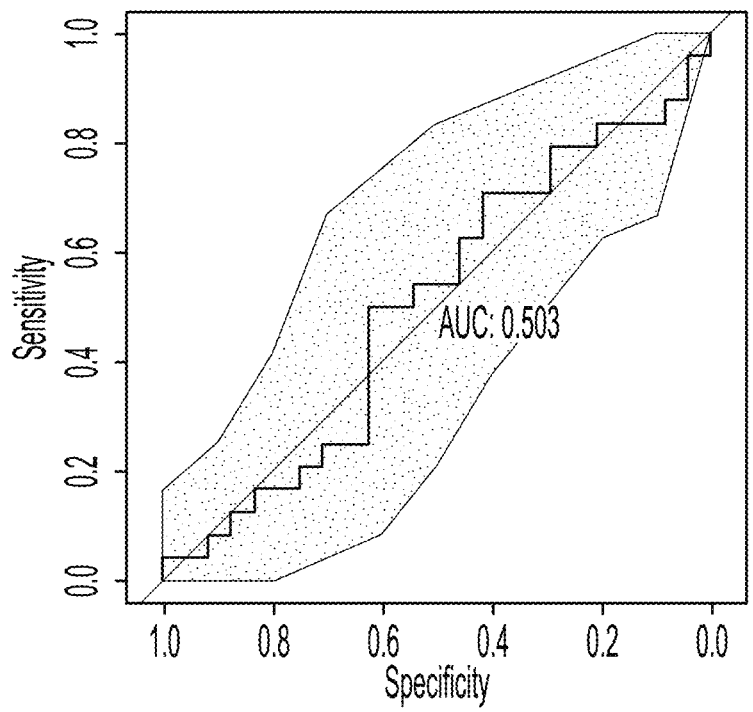
FIG. 4 shows the same data from FIG. 1 analyzed using the International Breast Cancer Intervention Study (IBIS) model.
Figure 4:
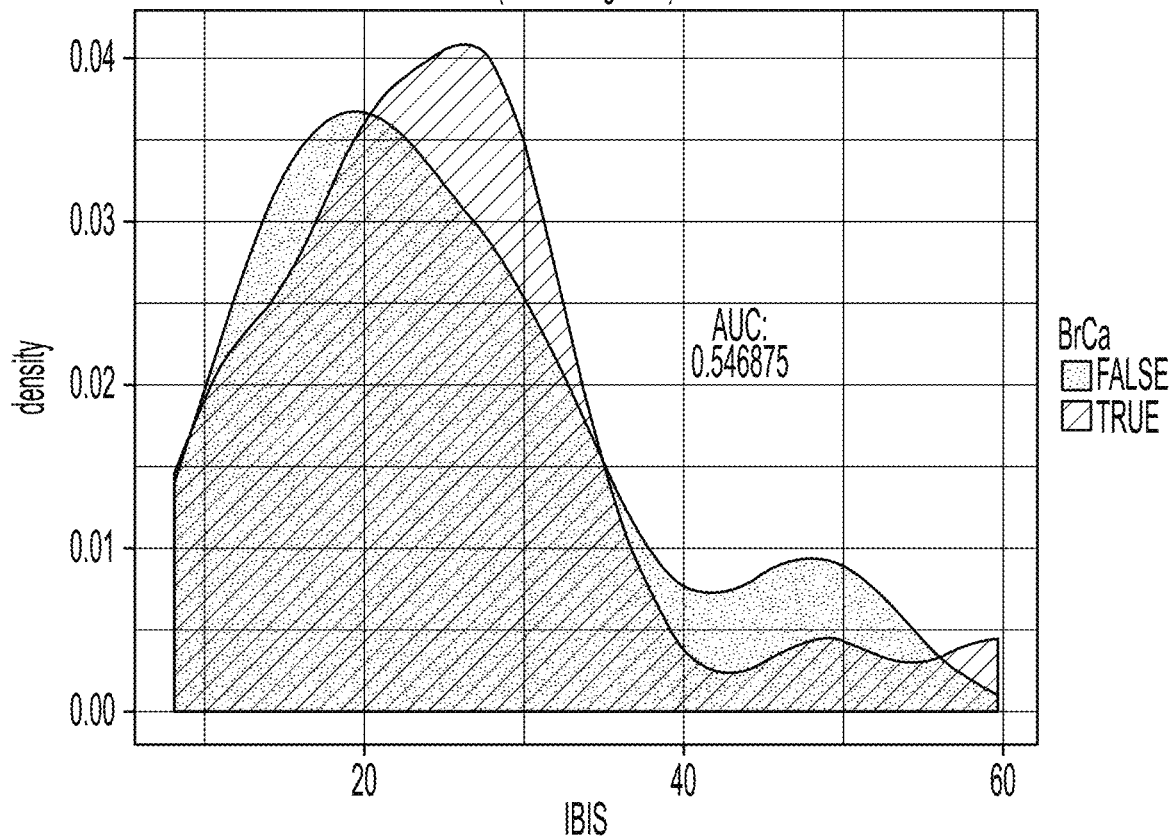

The tested miRNA signature of miR-3124-5p, miR-1184, miR-4423-3p, miR-4529-3p, miR-7855-5p, and miR-4446-3p performed better than current models with an AUC of 0.896 (CI 0.804-0.988) (see FIGS. 1-4). In published studies, the Gail model has been found to have a modest performance with an AUC of 0.55-0.62 (FIG. 2), while the Claus model appears to perform somewhat better with an AUC of 0.71 (FIG. 3). The IBIS model is thought to be a more generalizable model, given that family history, biopsy history, and other factors are included. Published studies demonstrate AUCs between 0.54-0.76 for this model (FIG. 4). A number of efforts have been made to improve the current models or develop new models with individualized factors such as breast density or single nucleotide polymorphisms (SNPs). These newer or refined models have shown small improvement, but accuracy remains (AUC<0.75). Given the high performance of this multi-miRNA signature, it would appear to have significant clinical applicability for risk prediction. The classification ability of each miRNA in the signature was lower (AUC ranging from 0.632 to 0.766) than that of the 6-miRNA signature together (AUC=0.896). The majority of published studies investigating use of miR-NAs in breast cancer have focused on the discriminatory value of single miRNAs. However, recent studies have recognized that a signature of several markers such as miRNAs will be less vulnerable to biological differences and therefore more valuable for clinical use.

These findings appear to represent the first miRNA signature associated with breast cancer risk. Among the 6 signature miRNAs detected in more than 25% of high-risk women in the present study, only miR-4446-3p was upregulated while the other 5 were found to be downregulated in cases as compared to controls. Published studies demonstrate that miR-1184 (expressed at the highest levels in the high-risk cohort), is located on the X chromosome but has not been studied in breast cancer. Circulating levels of miR-1184 are reported to be increased in patients with prostate cancer [Knyazev et al., Bull Exp Biol Med., 2016: 161: 108-11], but were decreased in breast cancer cases in the present cohort. MicroRNA-4423-3p has a role in regulating epithelial cell differentiation [Perdomo et al., Proc Natl Acad Sci, 2013; 110: 18946-51], is reduced in lung tumors, and downregulated in rheumatic heart disease [Li et al., Biomed Res Int, 2015; 2015: 524519].

Materials and Methods

Patient and Sample Identification:

The High-Risk Breast Program (HRBP) at the University of Vermont Cancer Center is a prospective cohort of women at increased risk for developing breast cancer due to one or more of the following risk factors: a strong family history, benign breast disease, prior irradiation for Hodgkin's disease, a known pathogenic mutation in a breast cancer-causing gene, and/or a modeled lifetime breast cancer risk of over 20% at time of enrollment. All participants were recruited from the high-risk breast clinic where they received screening recommendations according to individual risk and clinical guidelines. Enrollees provided written informed consent to be included in the HRBP database and re-contacted every 4 years thereafter for follow-up. At baseline and subsequent follow-up visits, blood samples were obtained and data collected via questionnaires and medical records to update reproductive and family histories, breast imaging results, lifestyle and health behaviors. Medical records and pathology reports were reviewed at each visit to ascertain incident breast cancers in the cohort. Serum was obtained from coagulated whole blood samples by centrifugation at miRNA Isolation Procedure:

Total RNA will be isolated using the miRNeasy Serum/Plasma kit (QIAGEN) following the manufacturer's protocol. An exact amount of a synthetic miRNA(cel-miR-39) will be spiked into each sample prior to organic extraction. To further increase sensitivity and technical reproducibility, many steps, including elution in a minimal volume or 14 L, are automated (QIAcube). Following isolation, RNA is stored in aliquots of appropriate size for downstream applications. Case/control sets will be processed together in the same isolation batch.

MicroRNA Detection and Quantitative PCR Analysis:

cDNA will be synthesized using the miScript RT II kit (QIAGEN) in batches of 5 cases with their 10 matched controls. Three miRNAs that are expressed at comparable levels in the 48 UVM cohort samples will be identified using the geNorm algorithm as potential endogenous controls. The expression of 25 candidate miRNAs for risk prediction, 3 endogenous control miRNAs, and spiked-in cel-miR-39 will be interrogated using miScript SYBR-Green quantitative PCR (QIAGEN). Each 384-well qPCR plate will assay 7 miRNAs and cel-miR-39 control across 5 cases and 10 matched controls. The delta-Ct method will be used to normalize miRNA expression levels to: 1) spiked-in celmiR-39 and 2) average of the 3 endogenous controls.

Calculation of miRNA-Based Breast Cancer Risk Score:

miRNA expression data will be merged with the case-control data set and used to calculate breast cancer risk scores. For each case and control, the risk score is equal to the summed products of 6 individual miRNA expression levels and their cognate score coefficients. Score coefficients will be derived from a multivariable Cox regression of case status on the 6 miRNA expression levels in the UVM HRBP cohort.

Statistical Analysis:

A conditional logistic regression model will be used to estimate the classification performance of the 6-miRNA risk score for segregating invasive breast cancer cases from controls. Conditioning on case-control strata will simultaneously adjust the modeled risk score coefficient for age and reason for high-risk status while addressing any selection bias induced by these matching factors. The dependent variable in these models will be invasive breast cancer status, and the sole independent variable will be the 6-miRNA risk score described above. The logistic model will be used to characterize the receiver operating characteristic (ROC) curve for the miRNA risk score. The ROC curve plots points at values of sensitivity and false-positive rate (1-specificity) for increasing values of a continuous test score. The area under the ROC curve (AUC; also referred to as the c-statistic), which is a measure of the classification accuracy afforded by a test score, will be calculated. The AUC, which ranges from 0.5 to 1, can be interpreted as the probability that the test score will be higher for the case than for the control in any randomly selected case/control pair. In addition to the ROC analysis, sensitivities and false-positive rates under a variety of risk score cut-points will be characterized. This exercise will help inform the utility of the risk score in the high-risk population—for example, by showing the maximum sensitivity that can be obtained while constraining the false-positive rate below an acceptable threshold.

The remaining 19 profiled miRNAs will be used to refine the risk score and improve its classification performance. To do this, new conditional logistic regression models will be fit with the expression levels of the 6 original miRNAs (instead of the calculated risk score) and score coefficients will be derived again. An iterative, stepwise forward-addition selection algorithm based on changes in AUC will be performed. To illustrate, the first step will be to add each of the 19 remaining miRNAs in turn to the 6-miRNA panel and evaluate the absolute increase in AUC to select the miRNA with the greatest impact on AUC. New miRNAs will be added to the model until the absolute change in AUC is negligible. Then, AUCs between the original 6-miRNA model and the newly constructed model will be statistically compared. Power calculations will be based on observed miRNA risk score distributions in cases and controls from the UVM HRBP cohort. Conservative estimates were made based on closer mean scores between groups—and higher standard deviations within groups—than was actually observed in the UVM HRBP cohort. The possibility that fewer than 39 cases will be available for analysis was also prepared for, given the potential for unsuitable blood samples or qPCR assay failure. Power estimates are based on 1,000 simulated data sets with different sets of score distribution characteristics and available sample sizes, and were carried out with the "aucsize" function for STATA. Assuming mean risk scores of 2.5 and 4 in the control and breast cancer groups, respectively, and a standard deviation of 2 in each group, it is estimated that there will be 86% power to detect a statistically significant (alpha=0.05) AUC of 0.70 with as few as 20 cases and 40 controls. The estimated power under the same score distribution parameters, but with 30 cases and 60 controls, is 95%. The difference in mean risk score in the UVM HRBP cohort was approximately 2.1, and the standard deviation in each group was near 1.0. Therefore, the power estimates are quite conservative, as they are based on a difference in mean risk score of 1.5 and within-group standard deviations of 2.0. There is ample power to detect an AUC of 0.70 (which is considerably smaller than the AUC observed in the UVM HRBP cohort) even with substantially fewer cases and controls than expected. It is expected that the model will yield an AUC >0.75, thus outperforming existing models. There is ample power to meet this objective.

Identification of Functional Significance of Signature miRNAs

Many of the miRNAs in the 6 miRNA signature have been linked to cancer, although their function in breast cancer is poorly characterized. Information is absent for one miRNA.

Mechanisms of regulation by these miRNAs are not well understood. Elucidating their roles in normal mammary epithelial and early stage tumor cells is essential for future application of these miRNAs to prevention efforts. Therefore, the functional roles of miRNAs in the risk signature will be studied in cell lines representing normal-like mammary epithelium (MCF10A, hMECs), premalignant cells (MCF10 DCIS), and early stage cancer (MCF7 ER$^+$ and MCF10AT1 ER$^-$). Each miRNA will be overexpressed and inhibited and the effects on proliferation, invasion, migration and tumorsphere formation will be quantified. Then, expression levels of miRNA-gene targets selected based on bioinformatics analyses of the miRNA targets and the enriched pathways (e.g. inflammation) related to breast cancer risk will be experimentally determined. These experiments will determine whether normal, precancerous or cancerous cells are most responsive to variation in expression of the signature's constituent miRNAs, and provide insight into their mechanism of action in breast cancer development.

FIGS. 7A-7B compare control and case serum miRNA levels (FIG. 7A) and miRNA levels secreted from near normal MCF10A mammary epithelial cells, malignant (MCF7ER+) and metastatic (MDA-MB-231 ER-) cells (FIG. 7B). High levels in normal cells are consistent with high level in control subjects. Cases which show a significant decrease in miRNAs-1184, -3124 (and a trend to lower levels for -4529), suggest these miRNAs are risk markers that can be monitored over time. PubMed, miRBase, and miRIAD were interrogated as sources for possible functional characterization of individual miRNAs as summarized in Table 1. The function of miR-4727-3p, one of the 25 high-performing miRNAs, is under examination because the comparison between cell and serum levels suggests this miRNA would be a strong risk predictor of ER positive breast cancer (FIGS. 7A-7B).

Correlation of Serum miRNAs with miRNAs Secreted from a Breast Cancer Progression Model Expression and inhibition of signature miRNA will alter biological properties of near normal breast epithelial and DCIS cells. Our priority is to initiate studies with MCF10A (normal-like mammary epithelia cells) and MCF10 DCIS (benign) as the best models for evaluating risk. Effects on proliferation, invasion, migration and tumorsphere formation will be assayed. Depending on results evaluating functional activities of signature miRNAs in these two cell lines, we will further confirm our findings with primary human mammary epithelial cells (hMECs) as well as with the malignant MCF10AT1 cell line. All studies will be performed in biological triplicates using sequential passages.

Expression Levels of Selected miRNA Gene Targets for Identification of Specific Cellular Mechanisms for Potential Intervention Targets of the 6 signature miRNAs were interrogated to identify associated biological pathways. The following breast cancer related pathways were found to be common to more than one signature miRNA: Inflammatory Mediator Regulation of TRP channels (miR-1184, -4529-3p, 7855-5p, 4423-3p, 4446-3p); Tyrosine Metabolism (miR-1184, -4423-3p, 4446-3p), associated with signaling pathways; Pantothenate and CoA Biosynthesis, reflecting adipose tissue metabolism (miR-1184, 4529-3p, 7855-5p); Thyroid Hormone Synthesis, a known factor linked to breast cancer (miR-1184, 4423-3p, 4446-3p, 4529-3p); Prostate Cancer (miR-1184, -4446-3p, 4529-3p, 7855-5p). Expression levels of common gene targets will be experimentally addressed in each of the enriched cancer-related pathways in multiple cell lines.

Materials and Methods

Figure 8B:
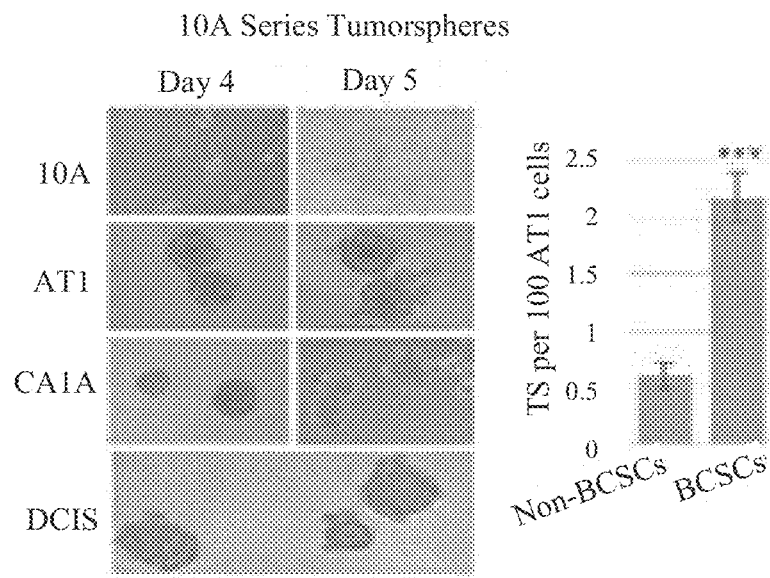

Cell Models and Properties:

The experimental design will test miRNA function in near normal mammary epithelial cells (MCF10A), human mammary epithelial cells (hMEC), cells representing the earliest premalignant stage ductal carcinoma in situ of the breast (MCF10DCIS.com), and if necessary, malignant MCF10AT1 cells. Currently a cell line of atypical ductal hyperplasia (ADH) is not available. Known miRNAs were reported in ADH tissue samples. It is anticipated that the normal MCF10A and MCF10DCIS cells will respond to inhibition and expression of the signature miRNAs (FIGS. 8A-8B). DCIS cells are enriched in cancer stem cells that exhibit EMT plasticity, which contributes to tumor initiation and recurrence and is related to clinical subtypes. The lab has performed RNA-Seq data for the MCF-progression series of cells (-10A, -AT1 and -CA1). Currently RNA-Seq DCIS data is being analyzed to identify expressed and silenced genes in these cells that will be compared with gene targets (mRNAs) of the signature miRNAs. This information will guide selection of altered genes upon exogenous expression or inhibition of the miRNA for qPCR validation.

Cell Treatments:

Cells are transfected after plating at 70% confluency with miRVana (Ambion) miRNA mimics or inhibitors and negative controls at a final concentration of 50 nmol/L in OPTI-MEM using Oligofectamine Reagent (Invitrogen). Fresh media is added 4 hours later and cells are harvested 72 hours later. Methods are detailed in many of publications for the following functional assays. Effects on proliferation are monitored starting 24 hours after transfection of miRNA reagents, collecting cells every 24 hours until confluency is reached (~3-4 days later). DNA damage (by phosphorylated histone H2AX, a marker of DNA double stranded breaks and apoptosis (by caspase 3) will be monitored, collecting cell layers at the 72 hour time point for Western blot and/or immunohistochemistry.

Cancer Promoting Properties:

Migration is assessed by wound-healing/scratch assay with closure rate monitored by live cell imaging and quantification with ImageJ software. Invasion assays use the transwell system with and without basement membrane coating on 8 am pore filters (Cell BioLabs) in serum-free media.

Figure 8C:
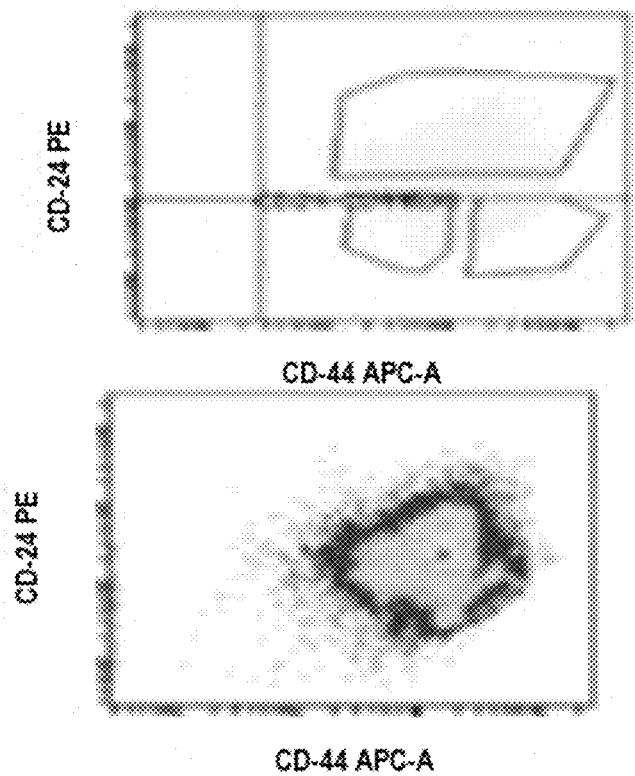

Mammosphere Assays:

An important assay for identifying clonal growth of abnormal premalignant cells (cancer stem cells (CSC) or DCIS cells) is efficiency in forming mammospheres and tumorspheres (TS). This quantitative assay for TS formation is a characteristic of CSCs and used as a measure of self-renewal capacity in pre-malignant breast cancer cells (FIG. 8A-8C). DCIS cells are highly associated with CSCs and form mammospheres as robust as the tumorspheres inmalignant AT1 cells (FIG. 8B). Plasticity between normal mammary cell and the cancer stem cell is an emerging concept; and thus inhibition or expression of a signature miRNA may promote normal cells in acquiring CSC-like properties. TS cultures are carried out on ultra-low attachment plates (Corning) using MammoCult medium (StemCell Technologies). TSs are counted on an inverted phase-contrast microscope (Leica) and mammosphere forming efficiencies (MFE %) are calculated (# of mammospheres per well/2000 cells seeded per well)×100 (FIG. 8B).

Gene Expression/Mechanisms:

Cell layers are collected for qPCR expression using primers for a panel of genes representing EMT markers, inducers of early stage cancer cells in 3 biological replicates (TGFB, Notch, B3 integrin, Wnt signaling), tumor growth and invasion genes (VEGF, MMP9, MMP13), various transcriptional regulators, and tumor suppressors. Approximately 35 genes representing the enriched pathways of the signature miRNAs will be added to elucidate mechanisms.

Clinical Relevance:

Constant surveillance of cancer related databases (e.g., The Cancer Genome Atlas' (TCGA) data portal, PubMed, ENCODE, and GSEO) will be continued. Targets revealed from the datasets will be examined in cBioPortal, TCGA, and Molecular Taxonomy of Breast Cancer International Consortium (METABRIC). These databases will be interrogated for correlations of the miRNAs and their involved target genes with clinical subtypes, clinical risk factors and survival data.

Expected Outcomes:

It is expected that miRNAs highly expressed in MCF10A cells and decreased in tumor cells are protecting mammary epithelial cells from the EMT; inhibition of miR4529-3p should significantly promote a cancer phenotype (i.e., increase in tumorsphere formation and acquisition of properties of DCIS cells (FIG. 8B)). Loss of these miRNAs over time in unaffected individuals would indicate that the miRNA is a validated risk factor and could be targeted for prevention (based on our data). MicroRNAs with low expression in controls and high expression in cases (years prior to diagnosis), (e.g., miR-4727-3p (FIG. 7A)) would also be considered a miRNA useful as a screening tool. A similar event may occur when a miRNA is expressed at low levels in normal mammary epithelial cells and the miRNA is exogenously expressed. It will be important to confirm phenotype of CSC-like cells by screening for CSC cell surface markers (CD24low/CD44high, ALDH1, CD49, CD133) by analytic flow cytometry (BD LSR II) in response to inhibition or expression of a signature miRNA. Later studies will elucidate functional roles and gene targets of signature miRNAs in MCF10A and early stage tumor cells. This analysis will reveal cellular mechanisms contributing to cancer risk that are essential for a precision based risk assessment and can be targeted for future intervention strategies to suppress the miRNA-mRNA risk factor(s).

Tables

TABLE 1

AUC for Individual and Signature miRNA

| MicroRNA | AUC | 95% CI | Predicted/Known Function |
|---|---|---|---|
| hsa-miR-3124-5p | 0.750 | 0.620-0.880 | Melanoma and gynocological tract |
| hsa-miR-1184 | 0.727 | 0.584-0.871 | Increased in prostate cancer, BPH, and colon |
| hsa-miR-4423-3p | 0.669 | 0.513-0.825 | Reduced in lung tumors |
| hsa-miR-4529-3p | 0.635 | 0.474-0.797 | Not characterized; Novel |
| hsa-miR-7855-5p | 0.635 | 0.476-0.795 | Associated with platelets and inflammation |
| hsa-miR-4446-3p | 0.632 | 0.496-0.768 | Upregulated in breast cancer cells |
| 6-miRNA signature | 0.896 | 0.804-0.988 | |

TABLE 2

Participant Characteristics (n = 48)

| | Affected cases (n = 24) | Cancer-free controls (n = 24) |
|---|---|---|
| Median age at blood draw[a] (range) | 55.4 (33.9-77.5) | 55.1 (32.8-78.4) |
| Risk factor[a] n (%) | | |
| Benign breast disease | 8 (33.3) | 8 (33.3) |
| Family history | 16 (66.7) | 16 (66.7) |
| Median modeled lifetime risk score (range) | | |
| Gail model (n = 40) | 18.4 (8.3-34.3) | 19.4 (8.7-52.9) |
| Claus model (n = 39) | 14.1 (5.0-35.8) | 10.7 (5.5-27.7) |
| IBIS model (n = 48) | 24.2 (8.1-59.6) | 22.0 (10.4-49.7) |
| Mammographic density at blood draw n (%) | | |
| <25% (entirely fatty) | 4 (16.7) | 1 (4.2) |
| 25-50% (scattered fibroglandular) | 9 (37.5) | 13 (54.2) |
| 51-75% (heterogeneously dense) | 11 (45.8) | 9 (37.5) |
| >75% (extremely dense) | 0 (0) | 1 (4.2) |
| Ethnicity n (%) | | |
| White | 24 (100) | 24 (100) |
| Median BMI (range) | 25.2 (19.1-55.6) | 25.0 (20.0-40.2) |
| Charlson comorbidity index n (%) | | |
| 0 | 14 (58.3) | 19 (79.2) |
| 1 | 9 (37.5) | 4 (16.7) |
| 2 and 3 | 1 (4.17) | 1 (4.17) |

[a]Matching factor

TABLE 3

Pathologic features of breast cancer (n = 24)

| | Median (range) | n (%) |
|---|---|---|
| Years of age at diagnosis | 56.9 (35.8-79.5) | |
| ≤50 | | 7 (29.2) |
| 51-59 | | 7 (29.2) |
| ≥60 | | 10 (41.7) |
| No. years between blood draw and cancer diagnosis | 3.2 (0.6-8.7) | |
| Tumor size | | |
| T1 (≤2 cm) | | 21 (87.5) |
| T1a (≤0.5 cm) | | 3 (12.5) |
| T1b (>0.5, ≤1 cm) | | 9 (37.5) |
| T1c (>1, ≤2 cm) | | 9 (37.5) |
| T2 (>2 cm, ≤5 cm) | | 2 (8.3) |
| T3 (>5 cm) | | 1 (4.2) |
| Lymph node stage (surgical) | | |
| N0 | | 21 (87.5) |
| N1[a] | | 2 (8.3) |
| N2 | | 1 (4.2) |
| Differentiation | | |
| Well | | 5 (20.8) |
| Moderate | | 14 (58.3) |
| Poor | | 5 (20.8) |
| Histology | | |
| Ductal Carcinoma | | 18 (75.0) |
| Lobular Carcinoma | | 4 (18.2) |
| Mucinous Carcinoma | | 1 (4.2) |
| Tubular Carcinoma | | 1 (4.2) |

TABLE 3-continued

Pathologic features of breast cancer (n = 24)

| | Median (range) | n (%) |
|---|---|---|
| Hormone receptors (ER and/or PR) | | |
| Positive | | 22 (91.7) |
| Negative | | 2 (8.3) |
| HER2 | | |
| Positive | | 4 (16.7) |
| Negative | | 19 (79.2) |
| Not assessed | | 1 (4.5) |

N0: Cancer not seen in axillary lymph nodes.
N1: Cancer spread to 1-3 axillary lymph nodes.
N2: Cancer spread to 4-9 axillary lymph nodes.
Tumors were classified as hormone-receptor positive if greater than 10% of cells were positive.
[a] All areas of cancer found in these subjects' lymph nodes were micrometastases.

TABLE 4 miRNA Data from UVM Cohort

| | Coefficient | p-value | # of models (out of 1000) | # of patients present in |
|---|---|---|---|---|
| hsa-miR-3124-5p | −1.062 | 5.30E−05 | 817 | 23 |
| hsa-miR-1184 | −0.32 | 0.01044 | 557 | 47 |
| hsa-miR-4423-3p | −0.33 | 0.00946 | 619 | 44 |
| hsa-miR-4529-3p | 0.621 | 0.00029 | 674 | 39 |
| hsa-miR-7855-5p | −0.626 | 2.40E−05 | 663 | 41 |
| hsa-miR-4446-3p | 0.359 | 0.01243 | 622 | 17 |
| hsa-miR-1184 | −0.274 | 0.00998 | 575 | 47 |
| hsa-miR-766-3p | −1.305 | 0.00021 | 779 | 11 |
| hsa-miR-4423-3p | −0.393 | 0.00174 | 793 | 44 |
| hsa-miR-4727-3p | 0.601 | 0.02527 | 672 | 8 |
| hsa-miR-208a-5p | 0.229 | 0.07624 | 617 | 4 |

TABLE 5

Candidate miRNA Sequences

| Candidate miRNA | miRBase Accession No. | mature miRNA sequence | SEQ ID NO: |
|---|---|---|---|
| hsa-miR-1184 | MIMAT0005829 | CCUGCAGCGACUUGAUGGCUUCC | 1 |
| hsa-miR-1226-5p | MIMAT0005829 | CCUGCAGCGACUUGAUGGCUUCC | 2 |
| hsa-miR-1468-3p | MIMAT0026638 | AGCAAAAUAAGCAAAUGGAAAA | 3 |
| hsa-miR-208a-5p | MIMAT0026474 | GAGCUUUUGGCCCGGGUUAUAC | 4 |
| hsa-miR-216b-5p | MIMAT0004959 | AAAUCUCUGCAGGCAAAUGUGA | 5 |
| hsa-miR-30d-5p | MIMAT0000245 | UGUAAACAUCCCCGACUGGAAG | 6 |
| hsa-miR-3124-5p | MIMAT0014986 | UUCGCGGGCGAAGGCAAAGUC | 7 |
| hsa-miR-3141 | MIMAT0015010 | GAGGGCGGGUGGAGGAGGA | 8 |
| hsa-miR-320d | MIMAT0006764 | AAAAGCUGGGUUGAGAGGA | 9 |
| hsa-miR-3613-3p | MIMAT0017991 | ACAAAAAAAAAAGCCCAACCCUUC | 10 |
| hsa-miR-3942-5p | MIMAT0018358 | AAGCAAUACUGUUACCUGAAAU | 11 |
| hsa-miR-4423-3p | MIMAT0018936 | AUAGGCACCAAAAAGCAACAA | 12 |
| hsa-miR-4446-3p | MIMAT0018965 | CAGGGCUGGCAGUGACAUGGGU | 13 |
| hsa-miR-4499 | MIMAT0019035 | AAGACUGAGAGGAGGGA | 14 |
| hsa-miR-4529-3p | MIMAT0019068 | AUUGGACUGCUGAUGGCCCGU | 15 |
| hsa-miR-4530 | MIMAT0019069 | CCCAGCAGGACGGGAGCG | 16 |
| hsa-miR-4668-5p | MIMAT0019745 | AGGGAAAAAAAAAAGGAUUUGUC | 17 |
| hsa-miR-4727-3p | MIMAT0019848 | AUAGUGGGAAGCUGGCAGAUUC | 18 |
| hsa-miR-4749-3p | MIMAT0019886 | CGCCCUCCUGCCCCCACAG | 19 |
| hsa-miR-4801 | MIMAT0019980 | UACACAAGAAAACCAAGGCUCA | 20 |
| hsa-miR-6732-5p | MIMAT0027365 | UAGGGGUGGCAGGCUGGCC | 21 |
| hsa-miR-766-3p | MIMAT0003888 | ACUCCAGCCCCACAGCCUCAGC | 22 |
| hsa-miR-7855-5p | MIMAT0030430 | UUGGUGAGGACCCCAAGCUCGG | 23 |

TABLE 5-continued

Candidate miRNA Sequences

| Candidate miRNA | miRBase Accession No. | mature miRNA sequence | SEQ ID NO: |
|---|---|---|---|
| hsa-miR-8075 | MIMAT0031002 | UGCUGAUGGCAGAUGUCGGGUCUG | 24 |
| hsa-miR-8084 | MIMAT0031011 | GAAUACUAAGUAAAAAAUCAGUA | 25 |

Other Embodiments

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art. Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed:

1. An array for determining a human patient's risk of developing a cancer, comprising oligonucleotide probes that hybridize to hsa-miR-4529-3p, hsa-miR-1184, hsa-miR-3141, hsa-miR-320d, hsa-miR-4423-3p, and hsa-miR-4530.

2. The array of claim 1, wherein the array further comprises oligonucleotide probes that hybridize to at least one additional cancer-associated miRNA selected from the group consisting of: hsa-miR-1226-5p, hsa-miR-1468-3p, hsa-miR-208a-5p, hsa-miR-216b-5p, hsa-miR-30d-5p, hsa-miR-3124-5p, hsa-miR-3613-3p, hsa-miR-3942-5p, hsa-miR-4446-3p, hsa-miR-4499, hsa-miR-4668-5p, hsa-miR-4727-3p, hsa-miR-4749-3p, hsa-miR-4801, hsa-miR-6732-5p, hsa-miR-766-3p, hsa-miR-7855-5p, hsa-miR-8075, and hsa-miR-8084.

3. A kit for determining a human patient's risk of developing cancer by detecting the presence of at least six cancer associated miRNAs in a biological sample, the kit comprising
engineered nucleic acids specific for hsa-miR-4529-3P, hsa-miR-1184, hsa-miR-3141, hsa-miR-320d, hsa-miR-4423-3p, and hsa-miR-4530,
wherein the engineered nucleic acids further comprise a detectable moiety and are detectable by a nucleic acid based detection assay,
a reagent for performing the nucleic acid based detection assay to detect the at least one cancer-associated miRNA using the nucleic acid, and
instructions for performing the nucleic acid based detection assay to detect the at least one cancer-associated miRNA.

4. The kit of claim 3, wherein the kit further comprises engineered nucleic acids specific for at least one additional cancer-associated miRNA selected from the group consisting of: hsa-miR-1226-5p, hsa-miR-1468-3p, hsa-miR-208a-5p, hsa-miR-216b-5p, hsa-miR- 30d-5p, hsa-miR-3124-5p, hsa-miR-3613-3p, hsa-miR-3942-5p, hsa-miR-4446-3p, hsa-miR-4499, hsa-miR-4668-5p, hsa-miR-4727-3p, hsa-miR-4749-3p, hsa-miR-4801, hsa-miR-6732-5p hsa-miR-766-3p, hsa-miR-7855-5p, hsa-miR-8075, and hsa-miR-8084.

5. The array of claim 2, wherein the array comprises oligonucleotide probes that hybridize to at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, or 25 cancer-associated miRNAs.

6. The array of claim 1, wherein the cancer is breast cancer.

7. The kit of claim 4, wherein the kit comprises nucleic acids for detecting at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, or 25 of the cancer-associated miRNAs.

8. The kit of claim 3, wherein the cancer is breast cancer.

9. The kit of claim 3, wherein the nucleic acid-based detection assay is an miRNA array assay.

10. The kit of claim 3, wherein the nucleic acid-based detection assay is a PCR assay.

11. The kit of claim 10, wherein the PCR assay is an RT-PCR assay or a quantitative PCR (qPCR) assay.

12. The kit of claim 3, wherein the nucleic acid-based detection assay is a multiplex miRNA profiling assay.

* * * * *